(12) United States Patent
Mitsuhashi et al.

(10) Patent No.: US 6,830,907 B2
(45) Date of Patent: Dec. 14, 2004

(54) MUTANTS OF MYCOBACTERIUM VACCAE-DERIVED FORMATE DEHYDROGENASE AND USES THEREOF

(75) Inventors: Kazuya Mitsuhashi, Niigata (JP); Hiroaki Yamamoto, Ibaraki (JP); Norihiro Kimoto, Ibaraki (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/996,008

(22) Filed: Nov. 28, 2001

(65) Prior Publication Data

US 2003/0157677 A1 Aug. 21, 2003

(30) Foreign Application Priority Data

Nov. 29, 2000 (JP) .................................... 2000-363894
Aug. 24, 2001 (JP) .................................... 2001-254631

(51) Int. Cl.⁷ ............................ C12N 9/04; C12N 9/02; C12N 15/00; C12P 19/36; C07H 21/04
(52) U.S. Cl. .................... 435/190; 435/189; 435/252.3; 435/90; 435/132; 435/440; 536/23.2
(58) Field of Search ................................ 435/189, 190, 435/252.3, 440, 90, 6; 536/23.2

(56) References Cited

PUBLICATIONS

Galkin et al., "Cloning of formate dehydrogenase gene from a methanol–utilizing bacterium *Mycobacterium vaccae* N10", Appl. Microbiol. Biotechnol., 44:479–483, 1995.

Slusarczyk et al., "Cloning and stabilization of NAD–dependent formate dehydrogenase from *Candida boidinii* by site–directed mutagenesis", Stability and Satilization of Bioactalysts, pp. 331–336, 1998.

Slusarczyk et al., "Stabilization of NAD–dependent formate dehydrogenase from *Candida buodinii* by site–directed mutagenesis of cysteine residues", Eur. J. Biochem. 267:1280–1289, 2000.

Tishkov et al., "Catalytic Properties and Stability of a *Pseudomonas SP.*101 Formate Dehydrogenase Mutants Containing CYS–255–SER and CYS–255–MET Replacements", Biochem. Biophys. Res. Comm., 192(2):976–981, 1993.

Demchenko et al., "The solvent effects on the kinetics of bacterial formate dehydrogenase reaction", *Biochimica et Biophysica Acta*, vol. 1039, No.3, 1990, pp. 290–296 (Abstract Only).

Galkin et al., "Conversion of alpha–keto acids to D–amino acids by coupling of four enzyme reactions", *Journal of Fermentation and Bioengineering*, vol. 83, No. 3, 1997, pp. 299–300 (Abstract Only).

Rojkova et al., "Bacterial formate dehydrogenase. Increasing the enzyme thermal stability by hydrophobization of alpha–helices", *FEBS*, 445, 1999, pp. 183–188.

Tishkov et al., "Directed mutagenesis of bacterial formate dehydrogenase: Role of cysteine–255 in the catalysis and stability of the enzyme", *Doklady Akademii Nauk*, vol. 328, No. 3, 1993, pp. 407–410 (Abstract Only).

Tishkov et al., "Pilot Scale Production and Isolation of Recombinant NAD⁺– and NADP⁺–Specific Formate Dehydrogenases", *Biotechnology and Bioengineering*, vol. 64, No. 2, Jul. 20, 1999, pp. 187–193.

*Primary Examiner*—P. Achutamurthy
*Assistant Examiner*—Yong D. Pak
(74) *Attorney, Agent, or Firm*—Fish & Richardson P.C.

(57) ABSTRACT

An objective of the present invention is to provide polypeptides capable of retaining a strong enzyme activity of formate dehydrogenase in the presence of an organic solvent and to provide the uses thereof.

Formate dehydrogenase mutant polypeptides, which are resistant to organic solvents, were constructed by substituting cysteines at position 146 and/or at position 256 in the amino acid sequence of *Mycobacterium vaccae*-derived formate dehydrogenase by site-directed mutagenesis. The polypeptides have strong activities of formate dehydrogenase in the presence of an organic solvent. The mutants are useful for the production of alcohols using ketones as raw material, etc.

66 Claims, 2 Drawing Sheets

SEQUENCE LISTING

<160> NUMBER OF SEQ ID NOS: 27

<210> SEQ ID NO 1
<211> LENGTH: 1206
<212> TYPE: DNA
<213> ORGANISM: Mycobacterium vaccae

<400> SEQUENCE: 1
atggcaaaag ttctgtgtgt tctttacgat gatccggtcg acggctaccc gaagacctat         60
gcccgcgacg atcttccgaa gatcgaccac tatccgggcg gccagatctt gccgacgccg        120

```
aaggccatcg acttcacgcc cgggcagttg ctcggctccg tctccggcga gctcggcctg    180
cgaccatatc tcgagtccaa cggccacacc ctggtcgtga cctccgacaa ggacggcccc    240
gactcggtgt cgagcgcga gctggtcgat gcggatgtcg tcatctccca gcccttctgg    300
ccggcctatc tgacgcccga gcgcatcgcc aaggccaaga acctgaagct cgcgctcacc    360
gccggcatcg gttccgacca cgtcgatctt cagtcggcta cgaccgcaa cgtcaccgtg    420 gcggaagtca cctactgcaa ctcgatcagc gtcgccgagc atgtggtgat gatgatcctg    480
tcgctggtgc gcaactatct gccctcgcac gaatgggcgc ggaagggcgg ctggaacatc    540
gccgactgcg tctcccacgc ctacgacctc gaggcgatgc atgtcggcac cgtggccgcc    600
ggccgcatcg tctcgcggt gctgcgccgt ctggcgccgt cgacgtgca cctgcactac    660 accgaccgtc accgcctgcc ggaatcggtc gagaaggagc tcaacctcac ctggcacgcg    720
acccgcgagg acatgtatcc ggtttgcgac gtggtgacgc tgaactgccc gctgcacccc    780
gaaaccgagc acatgatcaa tgacgagacg ctgaagctgt tcaagcgtgg cgcctacatc    840
gtcaacaccg cccgcggcaa gctgtgcgac cgcgatgccg tggcacgtgc gctcgaatcc    900
ggccggctgg ccggctatgc cggcgacgtg tggttcccgc agccggcgcc gaaggaccac    960
ccctggcgga cgatgcccta taacggcatg accccgcaca tctccggcac acgctgacc    1020 gcgcaggcgc gttatgcggc gggcacccgc gagatcctgg agtgcttctt cgagggccgt    1080
ccgatccgcg acgaatacct catcgtgcag gcggcgctc ttgccggcac cggcgcgcat    1140
tcctactcga agggcaatgc caccggcggt tcggaagagg ccgccaaatt caaaaaagcg    1200
gtctaa                                                               1206
```

<210> SEQ ID NO 2
<211> LENGTH: 401
<212> TYPE: PRT
<213> ORGANISM: Mycobacterium vaccae

<400> SEQUENCE: 2

```
Met Ala Lys Val Leu Cys Val Leu Tyr Asp Asp Pro Val Asp Gly Tyr
 1               5                   10                  15

Pro Lys Thr Tyr Ala Arg Asp Asp Leu Pro Lys Ile Asp His Tyr Pro
             20                  25                  30

Gly Gly Gln Ile Leu Pro Thr Pro Lys Ala Ile Asp Phe Thr Pro Gly
         35                  40                  45

Gln Leu Leu Gly Ser Val Ser Gly Glu Leu Gly Leu Arg Pro Tyr Leu
     50                  55                  60

Glu Ser Asn Gly His Thr Leu Val Val Thr Ser Asp Lys Asp Gly Pro
 65                  70                  75                  80

Asp Ser Val Phe Glu Arg Glu Leu Val Asp Ala Asp Val Val Ile Ser
                 85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175
```

```
Gly Trp Asn Ile Ala Asp Cys Val Ser His Ala Tyr Asp Leu Glu Ala
            180                 185                 190
Met His Val Gly Thr Val Ala Ala Gly Arg Ile Gly Leu Ala Val Leu
            195                 200                 205
Arg Arg Leu Ala Pro Phe Asp Val His Leu His Tyr Thr Asp Arg His
            210                 215                 220
Arg Leu Pro Glu Ser Val Glu Lys Glu Leu Asn Leu Thr Trp His Ala
225                 230                 235                 240
Thr Arg Glu Asp Met Tyr Pro Val Cys Asp Val Val Thr Leu Asn Cys
                245                 250                 255
Pro Leu His Pro Glu Thr Glu His Met Ile Asn Asp Glu Thr Leu Lys
            260                 265                 270
Leu Phe Lys Arg Gly Ala Tyr Ile Val Asn Thr Ala Arg Gly Lys Leu
            275                 280                 285
Cys Asp Arg Asp Ala Val Ala Arg Ala Leu Glu Ser Gly Arg Leu Ala
            290                 295                 300
Gly Tyr Ala Gly Asp Val Trp Phe Pro Gln Pro Ala Pro Lys Asp His
305                 310                 315                 320
Pro Trp Arg Thr Met Pro Tyr Asn Gly Met Thr Pro His Ile Ser Gly
                325                 330                 335
Thr Thr Leu Thr Ala Gln Ala Arg Tyr Ala Ala Gly Thr Arg Glu Ile
            340                 345                 350
Leu Glu Cys Phe Phe Glu Gly Arg Pro Ile Arg Asp Glu Tyr Leu Ile
            355                 360                 365
Val Gln Gly Gly Ala Leu Ala Gly Thr Gly Ala His Ser Tyr Ser Lys
            370                 375                 380
Gly Asn Ala Thr Gly Gly Ser Glu Glu Ala Ala Lys Phe Lys Lys Ala
385                 390                 395                 400
Val

<210> SEQ ID NO 3
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 3
cttcctagag gaattcaacc atggcaaaag ttctgtgtgt tc                      42

<210> SEQ ID NO 4
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 4
cagtctagat tagaccgctt ttttgaattt ggcg                               34

<210> SEQ ID NO 5
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 5
```

```
taatctagag gaattcaata atggatccaa caatgacgtt tc                             42
```

<210> SEQ ID NO 6
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 6

```
tagaagctta agctattaaa cgcaagtgta cccac                                    35
```

<210> SEQ ID NO 7
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 7

```
ctttctagag gaattcaacc atggcaaaag ttctgtctgt tc                             42
```

<210> SEQ ID NO 8
<211> LENGTH: 49
<212> TYPE: DNA
<213> ORGANISM: Artificial Sequence
<220> FEATURE:
<223> OTHER INFORMATION: Artificially synthesized primer sequence

<400> SEQUENCE: 8

```
gtatccggtt tgcgacgtcg tgacgctgaa ctccccgctg caccccgaa                     49
```

<210> SEQ ID NO 9
<211> LENGTH: 49
<212> TYPE: DNA
<213> ORGANISM: Artificial Sequence
<220> FEATURE:
<223> OTHER INFORMATION: Artificially synthesized primer sequence

<400> SEQUENCE: 9

```
ttcggggtgc agcggggagt tcagcgtcac gacgtcgcaa accggatac                     49
```

<210> SEQ ID NO 10
<211> LENGTH: 33
<212> TYPE: DNA
<213> ORGANISM: Artificial Sequence
<220> FEATURE:
<223> OTHER INFORMATION: Artificially synthesized primer sequence

<400> SEQUENCE: 10

```
cggaagtcac ctactcaaac tcgatcagcg tcg                                      33
```

<210> SEQ ID NO 11
<211> LENGTH: 33
<212> TYPE: DNA
<213> ORGANISM: Artificial Sequence
<220> FEATURE:
<223> OTHER INFORMATION: Artificially synthesized primer sequence

<400> SEQUENCE: 11

```
cgacgctgat cgagtttgag taggtgactt ccg                                      33
```

<210> SEQ ID NO 12
<211> LENGTH: 33
<212> TYPE: DNA
<213> ORGANISM: Artificial Sequence

```
<220> FEATURE:
<223> OTHER INFORMATION: Artificially synthesized primer sequence

<400> SEQUENCE: 12
gacatgtatc cggtttctga cgtcgtgacg ctg                          33

<210> SEQ ID NO 13
<211> LENGTH: 33
<212> TYPE: DNA
<213> ORGANISM: Artificial Sequence
<220> FEATURE:
<223> OTHER INFORMATION: Artificially synthesized primer sequence

<400> SEQUENCE: 13
cagcgtcacg acgtcagaaa ccggatacat gtc                          33

<210> SEQ ID NO 14
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 14
cgagatcctg gagtcattct tcgaaggccg tccga                        35

<210> SEQ ID NO 15
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 15
tcggacggcc ttcgaagaat gactccagga tctcg                        35

<210> SEQ ID NO 16
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 16
atggcaaaag tttttagctgt tctttacgat                             30

<210> SEQ ID NO 17
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 17
atcgtaaaga acagctaaaa cttttgccat                              30

<210> SEQ ID NO 18
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 18
ggcaaatatt ctgaaatgag c                                       21
```

<210> SEQ ID NO 19
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 19
tcacgacgtc gcaaaccgga                                           20

<210> SEQ ID NO 20
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 20
atggcaaaag ttttagtagt tctttacgat                                30

<210> SEQ ID NO 21
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 21
atcgtaaaga actactaaaa cttttgccat                                30

<210> SEQ ID NO 22
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 22
gtgacgctga acgctccgct gcacccc                                   27

<210> SEQ ID NO 23
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 23
ggggtgcagc ggagcgttca gcgtcac                                   27

<210> SEQ ID NO 24
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 24
gtgacgctga acgttccgct gcacccc                                   27

<210> SEQ ID NO 25
<211> LENGTH: 27
<212> TYPE: DNA
<213> ORGANISM: Artificial Sequence
<220> FEATURE:
<223> OTHER INFORMATION: Artificially synthesized primer sequence

```
<400> SEQUENCE: 25 gggggtgcagc ggaacgttca gcgtcac                                              27

<210> SEQ ID NO 26
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 26
gaagtcacct acgctaactc gatcagc                                               27

<210> SEQ ID NO 27
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 27
gctgatcgag ttagcgtagg tgacttc                                               27
```

MUTANTS OF MYCOBACTERIUM VACCAE-DERIVED FORMATE DEHYDROGENASE AND USES THEREOF

TECHNICAL FIELD

The present invention relates to mutants of *Mycobacterium vaccae*-derived formate dehydrogenase, polynucleotides encoding the mutants, and a method for producing reduced form of β-nicotinamide adenine dinucleotide (NADH) from oxidized form of β-nicotinamide adenine dinucleotide (NAD$^+$) by using them.

BACKGROUND

Previously there has been a known method for producing optically active (S)-4-halo-3-hydroxybutyrate ester, which is an asymmetric reduction method (Unexamined Published Japanese Patent Application No. (JP-A) Sho 61-146191; JP-A Hei 6-209782, etc.) using microorganisms such as baker's yeast. However, the method has been industrially unusable, because multiple types of reductases are present in microbial cells and thus the optical purity and yield of the product are low. The optically active (S)-4-halo-3-hydroxybutyrate ester can be used as an intermediate for pharmaceuticals and such, and thus methods for obtaining optically pure enantiomer (synthesis or resolution) have been an industrially important challenge.

*Kluyveromyces aestuarii*-derived carbonyl reductase (JP-A 2000-236883) is known to generate (S)-4-halo-3-hydroxybutyrate ester from 4-haloacetoacetate ester. A method has been reported, for synthesizing (S)-4-halo-3-hydroxybutyrate ester by using this enzyme. However, a stoichiometric amount of reduced form of β-nicotinamide adenine dinucleotide (NADH) as a co-enzyme is required in the production of optically active alcohols by using this enzyme. The co-enzyme is extremely expensive, and therefore, on an industrial scale, it is economically disadvantageous to utilize the method where a required amount of the co-enzyme is just used. Thus it is important to repeatedly reuse the co-enzyme by reducing oxidized form of β-nicotinamide adenine dinucleotide (NAD$^+$) to NADH, to construct an economically advantageous process.

So far, there have been reports in which formate dehydrogenase (Methods in Enzymology 136:9–21, 1987) or glucose dehydrogenase (JP-A 2000-236883) is used to reduce the co-enzyme NAD$^+$ into NADH. However, glucose dehydrogenase converts glucose to gluconic acid, and as a result, there is a problem in which an equal amount of gluconic acid and optically active alcohol of interest is generated.

On the other hand, formate dehydrogenase converts formic acid into carbonic acid, and the generated carbonic acid is efficiently eliminated from the system being converted to a carbon dioxide. Thus the method can be an economically advantageous process. However, there is also a disadvantage in the use of formate dehydrogenase, i.e., the stability of this enzyme is not high enough and as a consequence it has a tendency to be inactivated. It is known that the inactivation depends on various factors, pH value, temperature, mechanical stress, ionic strength and type of ion in the substrate solution, heavy metals, oxidation of thiol group by oxygen, etc. (JP-A Hei 11-225784). In this context, there are reports on methods in which the following mutations are used to enhance the stability.

Tishkov et al. have shown that mutants of formate dehydrogenase from *Pseudomonas* sp. 101, in which the cysteine at position 256 has been substituted with serine or methionine by site-directed mutagenesis, have enhanced stability to mercury but reduced thermal stability (Biochem. Biophys. Res. Commun. 192:4480–4485, 1993). They have also reported mutants showing enhanced thermal stability, which were similarly created by substituting serine with alanine, valine, or leucine at position 131, 160, 168, 184, or 228 (FEBS Letters 445:183–188, 1999).

Slusarczyk et al. have shown that mutants of formate dehydrogenase from *Candida boidinii* created by site-directed mutagenesis, in which the cysteine at position 23 has been substituted with serine as well as cysteine at position 262 with valine or alanine, exhibit enhanced stability to copper, enhanced pH stability in the range of weak alkaline pH, but reduced thermal stability (Eur. J. Biochem. 267:1280–1289, 2000).

Despite these research efforts, there has been a problem to be solved, which is lower yield due to decreased activity of formate dehydrogenase during the production of the reduced products such as alcohols from the oxidized substrates such as ketones in conjunction with the regeneration of co-enzyme NADH by using the above enzyme.

SUMMARY

With consideration given to the situation, the present invention was achieved, and an objective of the present invention is to provide formate dehydrogenase of which activity is not lowered during the process of producing the reduced product from the oxidized substrate while co-enzyme NADH is being regenerated. In addition, another objective of the present invention is to efficiently produce reduced product from oxidized substrate by using such an enzyme.

In order to achieve the above objectives, the inventors first investigated causes of the decrease of formate dehydrogenase activity during the production process of the above-mentioned reduced product. Then the inventors found that formate dehydrogenase was rapidly inactivated in the presence of organic solvents, such as ketones, as raw materials. Thus the inventors made an effort to search mutants of formate dehydrogenase for those resistant to organic solvents or those of which activity is enhanced by organic solvents. The inventors eventually succeeded in the construction of mutants of formate dehydrogenase having the nature in which the activity has been enhanced in the presence of organic solvents as compared with that in the absence of organic solvent by modifying the cysteine residue at position 146 in *Mycobacterium vaccae*-derived formate dehydrogenase (SEQ ID NO:2), which were found through constructing a variety of mutants of formate dehydrogenase and searching them.

Furthermore, the inventors found that mutants of formate dehydrogenase showing the resistance to organic solvents were obtainable by modifying the cysteine at position 256.

Further the inventors have succeeded in the coexpression of formate dehydrogenase and carbonyl reductase in *E. coli* by constructing expression vectors containing polynucleotides encoding these mutant enzymes and polynucleotide encoding carbonyl reductase which reduces ketones into alcohols. The use of these expressed enzymes have made it possible to efficiently produce reduced product from oxidized substrate, e.g., ketones, and for example, to efficiently produce alcohols from the substrate, while co-enzyme NADH is being regenerated.

As described above, the inventors created formate dehydrogenase mutants that is resistant to organic solvents and of which activity is enhanced in the presence of an organic solvent, and found a method for efficiently producing reduced product of oxidized substrate from the substrate by coexpressing the enzyme and carbonyl reductase; thus the inventors completed the present invention.

Specifically, the present invention relates to the following polypeptides and a method for efficiently producing reduced product from oxidized substrate using the polypeptides.

1. A polypeptide having a strong activity of formate dehydrogenase in the presence of an organic solvent, said polypeptide comprising a mutation in which amino acids other than cysteine are substituted at least for cysteine residues at positions 146 and/or 256 in the amino acid sequence of SEQ ID NO:2.
2. The polypeptide of 1, wherein the substituted amino acid at position 146 is serine or valine.
3. The polypeptide of 1, wherein the substituted amino acid at position 256 is serine, alanine, or valine.
4. The polypeptide of 1, wherein said polypeptide comprises a mutation in which amino acids other than cysteine are substituted at least for cysteine residues at positions 146 and 256 in the amino acid sequence of SEQ ID NO:2.
5. The polypeptide of 4, wherein the substituted amino acid at position 146 is serine or valine, and the substituted amino acid at position 256 is serine, alanine, or valine.
6. The polypeptide of 1, wherein said polypeptide further comprises a mutation in which an amino acid other than cysteine is substituted for cysteine residue at position 6 in the amino acid sequence of SEQ ID NO:2.
7. The polypeptide of 6, wherein the substituted amino acid at position 6 is serine, alanine, or valine.
8. A polypeptide comprising the amino acid sequence of SEQ ID NO:2 that contains one or more mutations, wherein said amino acid sequence is selected from the group consisting of:
    (1) an amino acid sequence in which cysteines at positions 6, 146, and 256 have been substituted with serine;
    (2) an amino acid sequence in which cysteine at position 6 has been substituted with alanine, and cysteine at position 256 has been substituted with serine;
    (3) an amino acid sequence in which cysteine at position 6 has been substituted with valine, and cysteine at position 256 has been substituted with serine;
    (4) an amino acid sequence in which cysteine at position 6 has been substituted with serine, and cysteine at position 256 has been substituted with alanine;
    (5) an amino acid sequence in which cysteine at position 6 has been substituted with serine, and cysteine at position 256 has been substituted with valine;
    (6) an amino acid sequence in which cysteine at position 146 has been substituted with serine;
    (7) an amino acid sequence in which cysteine at position 256 has been substituted with serine;
    (8) an amino acid sequence in which cysteines at positions 146 and 256 have been substituted with serines;
    (9) an amino acid sequence in which cysteine at position 256 has been substituted with valine;
    (10) an amino acid sequence in which cysteine at position 146 has been substituted with serine, and cysteine at position 256 has been substituted with valine;
    (11) an amino acid sequence in which cysteine at position 6 has been substituted with alanine, and cysteine at position 256 has been substituted with valine;
    (12) an amino acid sequence in which cysteine at position 6 has been substituted with alanine, cysteine at position 146 has been substituted with serine, and cysteine at position 256 has been substituted with valine; and
    (13) an amino acid sequence in which cysteines at positions 6 and 146 have been substituted with alanines, and cysteine at position 256 has been substituted with valine.
9. A polynucleotide encoding the polypeptide of 1 or 8.
10. A vector into which the polynucleotide of 9 has been inserted.
11. The vector of 10, wherein a polynucleotide encoding a reductase has been further inserted into said vector.
12. The vector of 11, wherein said reductase is a carbonyl reductase derived from *Kluyveromyces aestuarii*.
13. A transformant containing the vector of 10.
14. The transformant of 13, wherein the transformant is a microorganism.
15. A method for producing the polypeptide of 1 or 8, said method comprising the step of culturing the transformant of 13.
16. A method for producing the polypeptide of 1 or 8 and a reductase, said method comprising the step of culturing a transformant containing the vector of 11.
17. The method of 16, wherein said reductase is a carbonyl reductase derived from *Kluyveromyces aestuarii*.
18. A method for producing reduced form of β-nicotinamide adenine dinucleotide from oxidized form of β-nicotinamide adenine dinucleotide, said method comprising the step of contacting any one of the following (a) to (c) with oxidized form of β-nicotinamide adenine dinucleotide:
    (a) the polypeptide of 1 or 8;
    (b) the transformant of 10; and
    (c) a processed product of the transformant of (b).
19. A method for producing a reduced product from an oxidized substrate, said method comprising the steps of:
    (1) producing reduced form of β-nicotinamide adenine dinucleotide by the method of 18; and
    (2) recovering a reduced product generated by contacting the reduced form of β-nicotinamide adenine dinucleotide of the step (1) and an oxidized substrate with a reductase that produces the reduced product from the oxidized substrate in the presence of the reduced form of β-nicotinamide adenine dinucleotide.
20. The method of 19, wherein said oxidized substrate is a ketone and said reduced product of the substrate is an alcohol.
21. The method of 20, wherein said ketone is 4-haloacetoacetate ester and said alcohol is (S)-4-halo-3-hydroxybutyrate ester.
22. The method of 19, wherein said reductase is *Kluyveromyces aestuarii*-derived carbonyl reductase.
23. The method of 19, wherein said reductase is produced by the method of 16. The details of one or more embodiments of the invention are set forth in the accompanying drawings and the description below. Other features, objects, and advantages of the invention will be apparent from the description and drawings, and from the claims.

DETAILED DESCRIPTION

Figure 1:
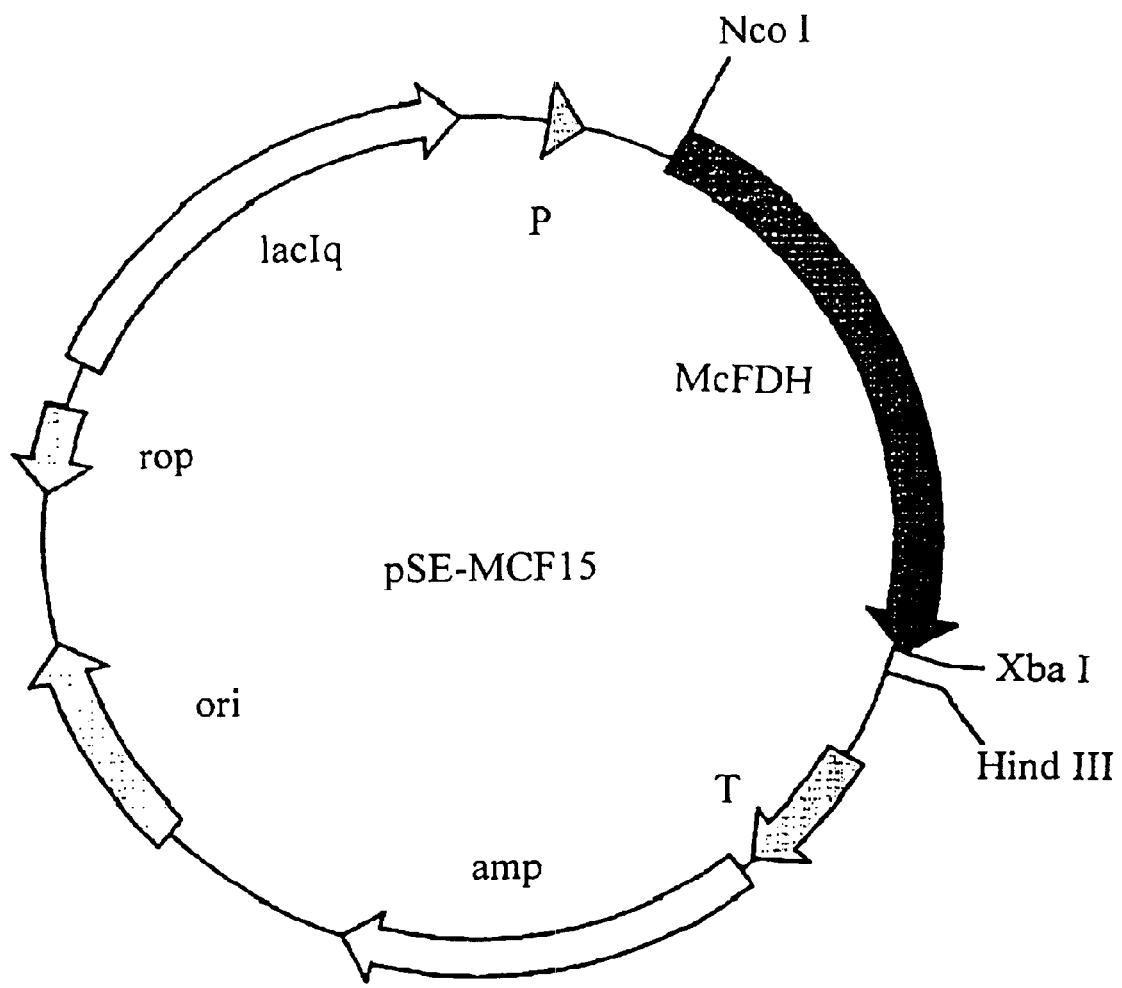
FIG. 1 shows the structure of plasmid pSE-MCF15.

The present invention provides mutants of formate dehydrogenase derived from *Mycobacterium vaccae*.

In one preferred embodiment of the present invention, the mutant is a mutant of *Mycobacterium vaccae*-derived formate dehydrogenase (SEQ ID NO:2) which contains at least a mutation where the cysteine at position 146 has been substituted with an amino acid other than cysteine (hereinafter referred to as "146 mutant"). The substituted amino acid at position 146 is preferably serine or valine. The 146 mutant may contain one or more amino acid mutations such as substitutions, deletions, additions and/or insertions at any positions other than position 146 in the amino acid sequence, as long as the cysteine at position 146 has been substituted with an amino acid other than cysteine. Such mutations can artificially be introduced or can be generated spontaneously. The mutants of the present invention include both types of mutants. The number of mutated amino acids in the 146 mutant are typically 50 amino acids or less, preferably 30 amino acids or less, and more preferably 10 amino acids or less (for example, 5 amino acids or less, 3 amino acids or less).

In the substantially pure polypeptide of the present invention, when there are mutations such as amino acid deletions, additions, or insertions at positions other than position 146 or 256, the position of cysteine residue counted from the N-terminus can be altered. In such cases, the polypeptide of the present invention can be produced by substituting amino acids other than cysteine at least for cysteines at positions in an altered amino acid sequence, where the positions are equivalent to position 146 and/or position 256 in SEQ ID NO:2. In other words, the polypeptide of the present invention includes a polypeptide having a strong activity of formate dehydrogenase in the presence of an organic solvent in which amino acids at equivalent positions to position 146 and/or position 256 in the amino acid sequence of SEQ ID NO:2 have been substituted with amino acids other than cysteine.

Such an equivalent position can be found by aligning an amino acid sequence around the cysteine with an amino acid sequence around a cysteine in SEQ ID NO:2. This type of operation is called alignment of amino acid sequences. An algorithm for preparing such an alignment is, for example, BLAST. Those skilled in the art can find equivalent amino acid positions in amino acid sequences of which lengths are different to one another based on the alignment.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel electrophoresis, or HPLC analysis.

As used herein, "percent identity" of two amino acid sequences or of two nucleic acids is determined using the algorithm of Karlin and Altschul (Proc. Natl. Acad. Sci. USA 87:2264–2268, 1990) modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. Homology search of protein can readily be performed, for example, in DNA Databank of JAPAN (DDBJ), by using the FASTA program, BLAST program, etc. BLAST protein searches are performed with the XBLAST program, score=50, wordlength=3. Where gaps exist between two sequences, Gapped BLAST is utilized as described in Altsuchl et al. (Nucleic Acids Res. 25:3389–3402, 1997). When utilizing BLAST and Gapped BLAST programs, the default parameters of the respective programs (e.g., XBLAST and NBLAST) are used.

An amino acid substitution is preferably mutated into different amino acid(s) in which the properties of the amino acid side-chain are conserved. A "conservative amino acid substitution" is a replacement of one amino acid residue belonging to one of the following groups having a chemically similar side chain with another amino acid in the same group. Groups of amino acid residues having similar side chains have been defined in the art. These groups include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The 146 mutant preferably has a strong activity of formate dehydrogenase in the presence of an organic solvent as compared with *Mycobacterium vaccae*-derived formate dehydrogenase (SEQ ID NO:2).

In the present invention, "strong activity of formate dehydrogenase" means the enzyme activity at least 70% or higher, for example, 80% or higher, preferably 90% or higher, more preferably 95% or higher in the presence of an organic solvent when compared with the enzyme activity in the absence of organic solvent. In natural formate dehydrogenase, only a low enzyme activity is recognized in the presence of organic solvents.

Further, in the present invention, "resistant to an organic solvent" means that the enzyme still retains the enzyme activity high enough even after the enzyme is placed in the presence of an organic solvent during a certain period of time. For example, the polypeptide of the present invention still retains 90% or higher enzyme activity after incubated in the presence of 20 μM ethyl 4-chloroacetoacetate at 25° C. for 20 minutes. The natural formate dehydrogenase may lose most of its enzyme activity under such conditions (8% or lower).

Further preferable mutants in accordance with the present invention can be enhanced in its enzyme activity in the presence of an organic solvent. In the present invention, the enhancement of the enzyme activity means that the enzyme activity in the presence of an organic solvent is 100% or higher, preferably 105% or higher, for example, 100 to 250% activity as compared with that in the absence of organic solvent. Furthermore, "in the presence of an organic solvent" means the presence of organic solvent of 1 μM or more, for example, 5 to 500 μM, specifically 5 to 50 μM, more specifically 10 to 30 μM, relative to an aqueous solvent.

Such organic solvents include, for example, acetate esters such as ethyl acetate, methyl acetate, and propyl acetate; acetoacetate esters such as ethyl acetoacetate and methyl acetoacetate; and 4-halo-3-oxobutyrate esters such as ethyl 4-chloroacetoacetate and methyl 4-chloroacetoacetate, but are not limited thereto.

The 146 mutant should have a strong activity of formate dehydrogenase in at least one organic solvent. Such formate dehydrogenase activity can be assayed by a method that is generally used by those skilled in the art. For example, such methods can include the following method. The enzyme is allowed to react in a reaction solution containing 100 mM potassium phosphate buffer (pH 7.0), 2.5 mM NAD$^+$, and 100 mM sodium formate at 25° C. to assay an increase in absorbance at 340 nm accompanying the increase in quantity of NADH. 1 U is defined as an amount of enzyme that is capable of catalyzing 1-$\mu$mol increase of NADH for 1 minute. Quantification of polypeptide is carried out by dye-binding using a protein assay kit from BioRad. When the substrate to be used is an organic solvent, particularly ethyl 4-chloroacetoacetate, instead of sodium formate, the change in absorbance at 340 nm is not recognizable under this condition.

In another preferable embodiment of the present invention, the mutant is a mutant of formate dehydrogenase derived from Mycobacterium vaccae (SEQ ID NO:2) which contains at least a mutation where the cysteine at position 256 has been substituted with an amino acid other than cysteine (hereinafter referred to as "256 mutant"). The substituted amino acid at position 256 is preferably serine, alanine or valine. The 256 mutant may contain one or more amino acid mutations such as substitutions, deletions, additions and/or insertions at any positions other than position 256 in the amino acid sequence, as long as the cysteine at position 256 has been substituted with an amino acid other than cysteine. Such mutations can artificially be introduced or can be generated spontaneously. The mutants of the present invention include both types of mutants. The number of mutated amino acids in the 256 mutant are typically 50 amino acids or less, preferably 30 amino acids or less, and more preferably 10 amino acids or less (for example, 5 amino acids or less, 3 amino acids or less).

The 256 mutant preferably shows high resistance to organic solvents as compared with Mycobacterium vaccae-derived formate dehydrogenase (SEQ ID NO:2). Such organic solvents include, for example, 4-halo-3-oxobutyrate esters such as 4-chloroacetoacetate ethyl ester, 4-bromoacetoacetate ethyl ester, 4-iodoacetate ethyl ester, methyl 4-chloroacetoacetate, propyl 4-chloroacetoacete; haloacetophenones such as chloroacetophenone and bromoacetophenone; and 3-halo-1-phenyl-2-propanone derivatives such as 3-chloro-1-phenyl-2-propanone and 3-bromo-1-phenyl-2-propanone, but are not limited thereto. The 256 mutant should show strong resistance to at least one organic solvent. The resistance of formate dehydrogenase to organic solvents, for example, to ethyl 4-chloroacetoacetate, can be assayed as follows.

A reaction solution which contains 100 mM potassium phosphate buffer (pH 7.0), 20 mM ethyl 4-chloroacetoacetate and formate dehydrogenase is incubated at 25° C. for 20 minutes, and then NAD$^+$ and sodium formate are added thereto at concentrations of 2.5 mM and 100 mM, respectively. After the reaction solution is incubated at 25° C., an increase of absorbance at 340 nm accompanying an increase in NADH is assayed. In a control experiment, after a reaction solution containing 100 mM potassium phosphate buffer (pH 7.0) and formate dehydrogenase is incubated at 25° C. for 20 minutes, NAD$^+$, sodium formate and ethyl 4-chloroacetoacetate are added at fmal concentrations of 2.5 mM, 100 mM, and 20 mM, respectively. The reaction solution is incubated at 25° C., and then an increase of absorbance at 340 nm accompanying an increase in NADH is assayed.

In still another preferable embodiment of the present invention, the mutant is a mutant of formate dehydrogenase derived from Mycobacterium vaccae (SEQ ID NO:2) which contains at least mutations where both the above-mentioned cysteines at position 146 and position 256 have been substituted with amino acids other than cysteine (hereinafter referred to as "146–256 mutant"). The substituted amino acid at position 146 is preferably serine or valine, and the substituted amino acid at position 256 is preferably serine, alanine or valine. There is no particular limitation on the type of mutation in the amino acid residue except the amino acid residues at position 146 and position 256, as long as both cysteine residues have been substituted with amino acids other than cysteine at position 146 and position 256.

The 146–256 mutant preferably has a strong activity of formate dehydrogenase in the presence of an organic solvent and shows high resistance to organic solvents as compared with Mycobacterium vaccae-derived formate dehydrogenase (SEQ ID NO:2).

In another embodiment of the present invention, the mutant is a mutant of the above formate dehydrogenase derived from Mycobacterium vaccae which contains a mutation where the cysteine at position 6 is substituted with an amino acid other than cysteine, in addition to the mutations at position 146 and/or position 256. The substituted amino acid at position 6 is preferably serine, alanine or valine. The mutant preferably has a strong activity of formate dehydrogenase in the presence of an organic solvent and/or shows high resistance to organic solvents as compared with Mycobacterium vaccae-derived formate dehydrogenase (SEQ ID NO:2).

Specific examples of preferable mutant of the present invention are shown below.

(a) A mutant of formate dehydrogenase derived from Mycobacterium vaccae, in which the cysteine at position 146 has been substituted with serine in the amino acid sequence of SEQ ID NO:2.

(b) A mutant of formate dehydrogenase derived from Mycobacterium vaccae, in which the cysteine at position 256 has been substituted with serine in the amino acid sequence of SEQ ID NO:2.

(c) A mutant of formate dehydrogenase derived from Mycobacterium vaccae, in which the cysteine at position 256 has been substituted with valine in the amino acid sequence of SEQ ID NO:2.

(d) A mutant of formate dehydrogenase derived from Mycobacterium vaccae, in which the cysteine at position 146 has been substituted with serine and the cysteine at position 256 has been substituted with serine in the amino acid sequence of SEQ ID NO:2.

(e) A mutant of formate dehydrogenase derived from Mycobacterium vaccae, in which the cysteine at position 146 has been substituted with serine and the cysteine at position 256 has been substituted with alanine in the amino acid sequence of SEQ ID NO:2.

(f) A mutant of formate dehydrogenase derived from Mycobacterium vaccae, in which the cysteine at position 146 has been substituted with serine and the cysteine at position 256 has been substituted with valine in the amino acid sequence of SEQ ID NO:2.

(g) A mutant of formate dehydrogenase derived from Mycobacterium vaccae, in which the cysteine at position 6 has been substituted with serine, the cysteine at position 146 has been substituted with serine and the cysteine at position 256 has been substituted with serine in the amino acid sequence of SEQ ID NO:2.

(h) A mutant of formate dehydrogenase derived from Mycobacterium vaccae, in which the cysteine at position 6 has been substituted with alanine and the cysteine at position 256 has been substituted with serine in the amino acid sequence of SEQ ID NO:2.

(i) A mutant of formate dehydrogenase derived from *Mycobacterium vaccae*, in which the cysteine at position 6 has been substituted with valine and the cysteine at position 256 has been substituted with serine in the amino acid sequence of SEQ ID NO:2.

(j) A mutant of formate dehydrogenase derived from *Mycobacterium vaccae*, in which the cysteine at position 6 has been substituted with serine and the cysteine at position 256 has been substituted with alanine in the amino acid sequence of SEQ ID NO:2.

(k) A mutant of formate dehydrogenase derived from *Mycobacterium vaccae*, in which the cysteine at position 6 has been substituted with serine and the cysteine at position 256 has been substituted with valine in the amino acid sequence of SEQ ID NO:2.

(l) A mutant of formate dehydrogenase derived from *Mycobacterium vaccae*, in which the cysteine at position 6 has been substituted with alanine, the cysteine at position 146 has been substituted with serine and the cysteine at position 256 has been substituted with valine in the amino acid sequence of SEQ ID NO:2.

(m) A mutant of formate dehydrogenase derived from *Mycobacterium vaccae*, in which the cysteine at position 6 has been substituted with alanine and the cysteine at position 256 has been substituted with valine in the amino acid sequence of SEQ ID NO:2.

(n) A mutant of formate dehydrogenase derived from *Mycobacterium vaccae*, in which the cysteine at position 6 has been substituted with alanine, the cysteine at position 146 has been substituted with alanine and the cysteine at position 256 has been substituted with valine in the amino acid sequence of SEQ ID NO:2.

Among the above mutants of (a) to (n), the mutant (a) shows high formate dehydrogenase activity in the presence of an organic solvent. The mutants of (b), (c), (h), (i), (j), (k) and (m) show strong resistance to organic solvents. The mutants of (d), (f), (g), (l) and (n) have strong activity of formate dehydrogenase in the presence of an organic solvent and are highly resistant to organic solvents.

The above mutants of the present invention can be obtained, for example, by modifying the amino acid sequence of *Mycobacterium vaccae*-derived formate dehydrogenase. These polypeptides can be prepared by a method that is generally used by those skilled in the art, for example, site-directed mutagenesis (Hashimoto-Gotoh, T. et al. (1995) Gene 152, 271–275; Zoller, M J, and Smith, M. (1983) Methods Enzymol. 100, 468–500). Specifically, they can be obtained by a method described below in Examples. The applicant has deposited *E. coli* (JM109(pSFR415)) containing pSFR415 shown in FIG. 2 and *E. coli* (JM109 (pSFR426)) containing pSFR426. Polynucleotides inserted in the plasmids are suitably used to prepare the mutants of the present invention.

The region around the cysteine residue at position 256 in *Mycobacterium vaccae*-derived formate dehydrogenase is a region conserved among other formate dehydrogenases. The cysteine at position 256 corresponds, for example, to cysteine at position 224 in the *Aspergillus nidulans* (which is called *Emericella nidulans* currently)-derived enzyme, cysteine at position 228 in the *Hansenula polymorpha* (which is called *Pichia angusta* currently)-derived enzyme (SWISS: P33677), cysteine at position 228 in the *Neurospora crassa*-derived enzyme (SWISS: NEUFDHA), and cysteine at position 255 in the *Pseudomonas* sp. 101-derived enzyme (SWISS: P33160).

In addition, the region around the cysteine residue at position 146 in *Mycobacterium vaccae*-derived formate dehydrogenase is also a region conserved among other formate dehydrogenases; for example, the residue corresponds to the cysteine residue at position 145 in the Pseudomonas sp. 101-derived enzyme (SWISS: P33160) (Appl. Microbiol. Biotechnol. 44:479–483, 1995). It is expectable to improve the organic solvent resistance and/or activation effect by organic solvents in these known enzymes through the modification by site-directed mutagenesis.

In addition, the present invention relates to isolated polynucleotides encoding mutants of formate dehydrogenase.

As used herein, an "isolated polynucleotide" is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide. Specifically excluded from this definition are polynucleotides of DNA molecules present in mixtures of different (i) DNA molecules, (ii) transfected cells, or (iii) cell clones; e.g., as these occur in a DNA library such as a cDNA or genomic DNA library.

Accordingly, in one aspect, the invention provides an isolated polynucleotide that encodes a polypeptide described herein or a fragment thereof. Preferably, the isolated polypeptide includes a nucleotide sequence that is at least 60% identical to the nucleotide sequence shown in SEQ ID NO:1. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO:1. In the case of an isolated polynucleotide which is longer than or equivalent in length to the reference sequence, e.g., SEQ ID NO:1, the comparison is made with the full length of the reference sequence. Where the isolated polynucleotide is shorter than the reference sequence, e.g., shorter than SEQ ID NO:1, the comparison is made to segment of the reference sequence of the same length (excluding any loop required by the homology calculation).

Polynucleotides encoding mutants of formate dehydrogenase in accordance with the present invention can be obtained, for example, by introducing nucleotide substitutions into the polynucleotide encoding *Mycobacterium vaccae*-derived formate dehydrogenase of SEQ ID NO:1 by site-directed mutagenesis that is generally used by those skilled in the art.

The present invention provides expression vector for formate dehydrogenase mutants by inserting a polynucleotide encoding the formate dehydrogenase mutant of the present invention, which is obtained by such a method, into a known expression vector. The formate dehydrogenase mutant of the present invention can be obtained as a recombinant polypeptide by culturing a transformant which has been transformed with the expression vector.

Further the present invention provides an expression vector for the formate dehydrogenase mutant and reductase, which can be prepared by inserting a polynucleotide encoding the formate dehydrogenase mutant of the present invention and a polynucleotide encoding reductase into a known expression vector. The formate dehydrogenase mutant of the present invention and reductase can be obtained as recombinant polypeptides by culturing transformants which have been transformed with the expression vector. Such a reductase is preferably a carbonyl reductase. Specifically, the reductase includes, for example, carbonyl reductases derived from the following microorganisms.

*Corynebacterium* sp. ST-10 (Appl. Environ. Microbiol. 63, 3783–3788, 1997)

*Candida parapsilosis* IFO 1396 (JP-A Hei 07-231785)

*Alcaligenes eutrophus* N9A (J. Bacteriol. 170, 5248–5256, 1988)

*Comamonas terrigena* (Biochim. Biophys. Acta 661, 74–86, 1981)

*Geotrichum candidum* IFO 4597 (Examined Published Japanese Patent Application (JP-B) No. Hei 01-27715)

*Hansenula ofunaensis* AKU 4328 (J. Biosci. Bioeng. 88, 148–152,1999)

*Nocardia erythropolis* ATCC 4277 (Appl. Environ. Microbiol. 61, 3729–3722, 1995)

*Nocardia fusca*

*Pichia* sp. NRRL-Y-11328 (J. Appl. Biochem. 3, 218–232, 1981)

*Pseudomonas* sp. PED (ATCC 49794) (U.S. Pat. No. 5,385,833)

*Rhodococcus erythropolis* DSM 743 (J. Biotechnol. 33, 283–292, 1994)

*Rhodococcus erythropolis* (Recl. Trav. Chim. Pays-Bas 115, 239–243, 1996)

*Rhodopseudomonas sphaeroides* (Tetrahedron Asym. 4, 1259–1269, 1993)

*Sulfolobus solfataricus* MT-4 (Biotechnol. Lett. 13, 31–34, 1991)

*Pichia finlandica* DSM 70280 (WO 01/61024)

In the present invention, there is no particular limitation on the type of microorganism to be used for the transformation to express the formate dehydrogenase mutant and/or reductase, as long as such a microorganism is capable of being transformed with a recombinant vector containing polynucleotide encoding the formate dehydrogenase mutant and/or polynucleotide encoding reductase and capable of expressing the formate dehydrogenase mutant and/or reductase. Methods for producing the formate dehydrogenase mutant of the present invention and/or reductase, which comprise such a transformant and the step of culturing the transformant, are also within the scope of the present invention. Available microorganisms as host organisms for the transformant include, for example, the following microorganisms:

Bacteria for which host-vector systems are developed, such as those belonging to the genus *Escherichia, Bacillus, Pseudomonas, Serratia, Brevibacterium, Corynebacterium, Streptococcus,* or *Lactobacillus;*

Actinomycetes for which host-vector systems are developed, such as those belonging to the genus *Rhodococcus* or *Streptomyces;*

Yeast for which host-vector systems are developed, such as those belonging to the genus *Saccharomyces, Kluyveromyces, Schizosaccharomyces, Zygosaccharomyces, Yarrowia, Trichosporon, Rhodosporidium, Pichia,* or *Candida;* and Fungi for which host-vector systems are developed, such as those belonging to the genus *Neurospora, Aspergillus, Cephalosporium,* or *Trichoderma.*

The procedure for generating transformants and constructing recombinant vectors suitable for hosts can be performed according to standard techniques known in the fields of molecular biology, bioengineering, and genetic engineering (for example, Sambrook et al., Molecular Cloning, Cold Spring Harbor Laboratories). To express the formate dehydrogenase mutant gene and/or reductase gene of the present invention in microorganism cells and such, first, the polynucleotide of the present invention is inserted into a plasmid vector or a phase vector stably existing in the microorganisms, and the genetic information is transcribed and translated. A promoter, which regulates transcription and translation, is inserted 5'-upstream of the polynucleotide of the present invention; preferably, a terminator is also inserted 3'-downstream of the polynucleotide. The promoter and terminator should function in microorganisms to be used as host cells. Vectors, promoters, and terminators functioning in various microorganisms are described in, for example, "Biseibutsugaku Kisokouza (Basic Course of Microbiology) Vol. 8 Idenshikougaku (Genetic Engineering), Kyoritsu Shuppan Co., Ltd., particularly for yeast, described in "Adv. Biochem. Eng. 43, 75–102 (1990), Yeast 8, 423–488 (1992)" etc.

For example, plasmid vectors such as pBR and pUC series, and promoters such as those of β-galactosidase (lac), tryptophan operon (trp), tac, trc (fusion of lac and trp), and those derived from λ-phage PL, PR, etc. can be used for the genus *Escherichia*, particularly *Escherichia coli*. Terminators derived from trpA, phage, and rrnB ribosomal RNA can also be used.

Vectors such as the pUB110 and pC194 series can be used for the genus *Bacillus* and can be integrated into chromosomes. Promoters and terminators such as those of alkaline protease (apr), neutral protease (npr), and amy (α-amylase) can be used.

Host-vector systems for the genus *Pseudomonas*, specifically *Pseudomonas putida* and *Pseudomonas cepacia*, have been developed. A broad host range vector pKT240 (containing genes necessary for autonomous replication derived from RSF1010) based on plasmid TOL that is involved in degradation of toluene compounds can be utilized. A promoter and terminator of a lipase (JP-A Hei 5-284973) gene and the like can be used.

Plasmid vectors such as pAJ43 (Gene 39:281, 1985) can be used for the genus *Brevibacterium*, especially *Brevibacterium lactofermentum*. Promoters and terminators for the genus *Escherichia* can be used for this microorganism.

Plasmid vectors such as pCS11 (JP-A Sho 57-183799) and pCB101 (Mol. Gen. Genet. 196:175, 1984) can be used for the genus *Corynebacterium*, particularly, *Corynebacterium glutamicum*.

Plasmid vectors such as pHV1301 (FEMS Microbiol. Lett., 26:239, 1985) and pGK1 (Appl. Environ. Microbiol. 50:94, 1985) can be used for the genus *Streptococcus*.

For the genus *Lactobacillus*, pAMβ1 developed for the genus *Streptococcus* (J. Bacteriol. 137:614, 1979) can be used, and some of the promoters for the genus *Escherichia* are applicable.

For the genus *Rhodococcus*, a plasmid vector isolated from *Rhodococcus rhodochrous* and such can be used (J. Gen. Microbiol. 138:1003, 1992).

Plasmids functioning in the genus *Streptomyces* can be constructed by the method described in "Genetic Manipulation of Streptomyces: A Laboratory Manual Cold Spring Harbor Laboratories by Hopwood et al. (1985)." For example, pIJ486 (Mol. Gen. Genet. 203:468–478, 1986), pKC1064 (Gene 103:97–99, 1991), and pUWL-KS (Gene 165:149–150, 1995) can be used, particularly for *Streptomyces lividans*. Such plasmids can also be used for *Streptomyces virginiae* (Actinomycetol. 11:46–53, 1997).

Plasmids such as the YRp, YEp, YCp, and YIp series can be used for the genus *Saccharomyces*, especially for *Saccharomyces cerevisiae*. Integration vectors (such as EP 537456) using homologous recombination with multiple copies of a ribosomal DNA in genomic DNA are extremely useful because they are capable of introducing multiple copies of genes into the host genome and stably maintaining the genes. Furthermore, promoters and terminators of alcohol dehydrogenase (ADH), glyceraldehyde-3-phosphate dehydrogenase (GAPDH), acid phosphatase (PHO), β-galactosidase (GAL), phosphoglycerate kinase (PGK), enolase (ENO), etc. can be used.

Plasmids such as the series of 2 μm plasmids derived from *Saccharomyces cerevisiae*, the series of pKD1 plasmids (J. Bacteriol. 145:382–390, 1981), plasmids derived from pGK11 involved in killer activity, the series of KARS plasmids containing an autonomous replication gene from the genus *Kluyveromyces*, and vector plasmids (such as EP 537456) capable of being integrated into chromosomes by homologous recombination with ribosomal DNA can be used for the genus *Kluyveromyces*, particularly for *Kluyveromyces lactis*. Promoters and terminators derived from ADH and PGK are applicable.

For the genus *Schizosaccharomyces*, plasmid vectors containing ARS (a gene involved in autonomous replication) derived from *Schizosaccharomyces pombe* and containing selective markers supplementing auxotrophy of *Saccharomyces cerevisiae* can be used (Mol. Cell. Biol. 6:80, 1986). Furthermore, ADH promoter derived from *Schizosaccharomyces pombe* is applicable (EMBO J. 6:729, 1987). In particular, pAUR224 is commercially available from Takara Shuzo.

For the genus *Zygosaccharomyces*, plasmid vectors such as pSB3 (Nucleic Acids Res. 13:4267, 1985) derived from *Zygosaccharomyces rouxii* can be used. Promoters of PHO5 derived from *Saccharomyces cerevisiae* and glycerolaldehyde-3-phosphate dehydrogenase (GAP-Zr) derived from *Zygosaccharomyces rouxii* (Agri. Biol. Chem. 54:2521, 1990), etc. are available.

A host-vector system has been developed for *Pichia angusta* (previous name: *Hansenula polymorpha*) among the genus *Pichia*. Usable vectors include *Pichia angusta*-derived genes (HARS1 and HARS2) involved in autonomous replication, but they are relatively unstable. Therefore, multi-copy integration of the gene into a chromosome is effective (Yeast 7:431–443, 1991). Promoters of AOX (alcohol oxidase) and FDH (formate dehydrogenase), which are induced by methanol and such, are also available. Host-vector systems for *Pichia pastoris* have been developed using genes such as PARS1 and PARS2 involved in autonomous replication derived from *Pichia* (Mol. Cell. Biol. 5:3376, 1985). Promoters such as a promoter of AOX with strong promoter activity induced by high-density culture and methanol are applicable (Nucleic Acids Res. 15:3859, 1987).

For the genus *Candida*, host-vector systems have been developed for *Candida maltosa, Candida albicans, Candida tropicalis, Candida utilis*, etc. Vectors for *Candida maltosa* using ARS, which was cloned from this strain, have been developed (Agri. Biol. Chem. 51:1587, 1987). Strong promoters for vectors that are able to be integrated into chromosomes have been developed for *Candida utilis* (JP-A Hei 08-173170).

In the genus *Aspergillus, Aspergillus niger* and *Aspergillus oryzae* have been most extensively studied. Plasmids able to be integrated into chromosomes are available. Promoters derived from extracellular protease and amylase are available (Trends in Biotechnology 7:283–287, 1989).

For the genus *Trichoderma*, host-vector systems based on *Trichoderma reesei* have been developed., and promoters derived from extracellular cellulase genes are available (Biotechnology 7:596–603, 1989).

Various host-vector systems for plants and animals, in addition to microorganisms, have been developed. In particular, expression systems for producing a large amount of foreign polypeptides in insects, particularly silkworms (Nature 315:592–594, 1985), and plants such as rape seeds, corns, and potatoes have been developed and are available.

Microorganisms capable of producing formate dehydrogenase mutants to be used in the present invention include mutant strains of *Mycobacterium vaccae* having the capability of producing mutants of formate dehydrogenase, variants thereof and transformed strains thereof, which have gained the capability of producing the enzyme of the present invention, created by using genetic manipulation.

Further the present invention provides a method for producing co-enzyme NADH (reduced form of β-nicotinamide adenine dinucleotide) from $NAD^+$ (oxidized form of β-nicotinamide adenine dinucleotide) using the formate dehydrogenase mutant of the present invention, a transformant of the present invention or a processed product of the transformant. The co-enzyme NADH is useful as a reduced co-enzyme for a variety of carbonyl reductases, alcohol dehydrogenases, aldehyde dehydrogenases, hydroxy acid dehydrogenases, and amino acid dehydrogenases; and thus it is an essential co-enzyme for the reducing activity of these enzymes.

In addition, the present invention provides a method for efficiently producing a reduced product, while regenerating NADH from $NAD^+$ that is produced during the production of the reduced product of oxidized substrate from the substrate by NADH-dependent reductase, via conversion reaction of formic acid to carbonic acid using the formate dehydrogenase mutant of the present invention. The NADH-dependent reductase is referred to an enzyme participating in the reduction using NADH as a co-enzyme, which can be, for example, an enzyme capable of catalyzing both reduction and oxidation, such as alcohol dehydrogenase. Further, in the above method, it is possible to use a transformant of the present invention or a processed product of the transformant instead of formate dehydrogenase mutant of the present invention.

The above-mentioned NADH-dependent reductase, oxidized substrate thereof, reduced product from the substrate include, for example, the following combinations, but are not limited thereto.

Production of alcohol from ketone by an enzyme (E.C. 1.1.1.-) producing alcohol using a carbonyl group as a substrate.

Production of aldehyde from carboxylic acid by an enzyme (E.C. 1.2.1.-) producing aldehyde using carboxylic acid as a substrate.

Production of carbon-carbon single bond-containing compounds from carbon-carbon double bond-containing compounds by an enzyme (E.C. 1.3.1.-) generating a carbon-carbon single bond via reduction of a carbon-carbon double bond.

Production of amino acid from keto acid by an enzyme (E.C. 1.4.1.-) generating an amino group via reductive amination using a carbonyl group as a substrate.

Production of diol from alkene by an enzyme (E.C. 1.14.12.-) generating diol via addition of oxygen to carbon-carbon double bond.

Here, enzymes classified into E.C. 1.1.1.-include, for example, alcohol dehydrogenase, D-hydroxy isocaproate dehydrogenase, L-hydroxy isocaproate dehydrogenase, D-mandelate dehydrogenase, L-mandelate dehydrogenase, D-lactate dehydrogenase, and L-lactate dehydrogenase. Enzymes classified into E.C. 1.2.1.-include, for example, aldehyde dehydrogenase. Enzymes classified into E.C. 1.3.1.-include, for example, enoyl-CoA reductase and fumarate reductase. Enzymes classified into E.C. 1.4.1.-include, for example, phenylalanine dehydrogenase, glutamate dehydrogenase, leucine dehydrogenase, and alanine dehydrogenase. Enzymes classified into E.C. 1.14.2.-include, for example, benzene dioxygenase.

There is no particular limitation on the type of substrate for these enzymes, as long as it is a compound on which the enzymes act. Such substrates include, for example, those containing intramolecular halogen, sulfur, and/or phosphorus, or the like; those containing hydroxyl group, amino group, or the like; those of which carbon chain is branched; those of which carbon chain is unsaturated; and those having aromatic ring including heterocyclic ring.

Since the formate dehydrogenase mutant of the present invention is resistant to organic solvents and/or activated by organic solvents, its activity can be kept for a long time and/or high enough for example even in the presence of ketones and alcohols; and thus it is advantageous in industrial process of alcohol production. In addition, there is no particular limitation on the type of carbonyl reductase, as long as it can generate alcohols from ketones using NADH as a co-enzyme. The enzyme reaction of interest can be achieved, by contacting the enzyme molecule, a processed product thereof, culture containing the enzyme molecules, or a transformant of microorganism and such producing the enzyme, with reaction solution. The transformant can be used in the form of the culture, cells separated from the culture medium by filtration, centrifugation or the like, or cells resuspended in buffer, water, or the like after they are separated by centrifugation and washed. The separated cells can be used in a state as they are recovered, as their disrupts, as treated with acetone or toluene, or as lyophilizate. When the enzyme is extracellularly produced, the culture medium of the transformant can also be used after it is separated from the transformant by the usual methods. The form of contacting the enzyme and reaction solution is not limited to these particular examples. The reaction solution is prepared by dissolving substrate and co-enzyme NADH required for the enzyme reaction in a solvent that is suitable for the enzyme activity. The processed product of microorganism containing a mutant of formate dehydrogenase in accordance with the present invention, or the processed product of microorganism containing carbonyl reductase specifically includes microorganism in which permeability of the cell membrane has been altered by a detergent or an organic solvent such as toluene as well as includes a cell-free extract obtained by disrupting cells of the microorganism with glass beads or enzyme treatment and partially purified material thereof.

There is no particular limitation on the type of ketone to be used as raw material for the production of alcohols in accordance with the present invention, as long as it can be reduced by a carbonyl reductase to be used. When carbonyl reductase from *Kluyveromyces aestuarii* is used, 4-haloacetoacetate ester is suitably used. Reduction of 4-haloacetoacetate ester results in the generation of (S)-4-halo-3-hydroxybutyrate ester. The halogen of 4-haloacetoacetate ester includes, for example, bromine, chlorine, iodine, or the like, and chlorine is preferably used in particular. The ester includes, for example, alcohol esters containing linear chain, branched chain, and aromatic substitution such as methyl ester, ethyl ester, propyl ester, isopropyl ester, butyl ester, octyl ester, and benzyl ester; ethyl ester is used most suitably. Derivatives of 4-haloacetoacetate ester include, for example, derivatives containing alkyl chain containing linear chain or branched chain at the second position, and halogen such as chlorine, bromine and iodine.

The reaction using the enzyme of the present invention can be performed in water, in water-insoluble organic solvent, for example, organic solvents such as ethyl acetate, butyl acetate, toluene, chloroform, cyclohexane, 1-octanol, n-hexane, and n-octane, or in a heterogeneous two-solvent system containing water solvent. In addition, it can be performed in a mixed solvent system which contains aqueous solvent such as buffer and water soluble solvent such as methanol, ethanol, isopropanol, acetonitrile, and acetone. The reaction can also be carried out in a reversed micelle system. Such a system includes, for example, isooctane/water reversed micelle system using Aerosol OT as a detergent.

The reaction of the present invention can be carried out, for example, by using immobilized enzyme, membrane reactor, etc. When the enzyme of the present invention, a processed product thereof, culture containing the enzyme molecules, or a transformant of microorganism and such producing the enzyme is intended to be immobilized, the immobilization can be achieved by a known method such as sulfur-containing polysaccharide (e.g., κ-carrageenan), calcium alginate, agar gel method, and polyacrylamide gel method.

Further, the reaction of the present invention can be performed under any reaction conditions as long as the conditions are those under which the enzyme of the present invention can work. The reaction can be conducted at a reaction temperature of 4 to 60° C., preferably 10 to 37° C.; at a pH of 3 to 11, preferably pH 5 to 8; at a substrate concentration ranging from 0.01 to 90%, preferably 0.1 to 30%. When the microbial cells or processed products thereof are intended to be used for the reaction, if desired, co-enzyme $NAD^+$ or NADH can be added at a concentration of 0.001 to 100 mM, preferably, 0.01 to 10 mM, to the reaction system. Further, the substrate can be added at the start of reaction, but it is preferable to add it continuously or stepwise so that the concentration of substrate does not become too high in the reaction mixture.

The purification of alcohol generated via reduction of ketone in accordance with the present invention can be performed by properly combining centrifugal separation of microbial cells and polypeptides, separation with membrane treatment or the like, extraction by solvent, distillation, crystallization, etc. For example, highly pure 4-halo-3-hydroxybutyrate ester can be purified by separating a reaction mixture containing microbial cells by centrifugation to eliminate the microbial cells, by removing polypeptides by ultrafiltration, by adding a solvent such as ethyl acetate or toluene to the filtrate for the extraction of 4-halo-3-hydroxybutyrate ester into the solvent layer, and then, after phase separation, by concentrating it under reduced pressure.

Provided by the present invention are mutants of formate dehydrogenase which are resistant to organic solvents and/or can be activated by organic solvents. The use of the enzyme of the present invention has made it possible to efficiently produce reduced form of β-nicotinamide adenine dinucleotide from oxidized form of β-nicotinamide adenine dinucleotide. Further, the effective regeneration of reduced form of co-enzyme β-nicotinamide adenine dinucleotide from the oxidized form by using the enzyme of the present invention has made it possible to produce alcohol in high yield in the process of production of alcohols from ketones mediated by carbonyl reductase.

Any patents, patent applications, and publications cited herein are incorporated by reference.

The present invention is illustrated in detail below with reference to Examples, but is not to be construed as being limited thereto.

Herein, "%" for concentration denotes weight per volume percent unless otherwise specified.

EXAMPLE 1
Subcloning of *Mycobacterium vaccae*-derived Formate Dehydrogenase The formate dehydrogenase was subcloned from plasmid pMcFDH(E-P) that has been described in a reference (Appl. Microbiol. Biotechnol. 44:479–483, 1995). Primers MCF-ATG2 (5'-CTTTCTAGAGGAATTCAACCATGGCAAAAGTTCTGTGTGTTC-3'/SEQ ID NO:3) and MCF-TAA3 (5'-CAGTCTAGATTAGACCGCTTTTTTGAATTTGGCG-3'/SEQ ID NO:4) were synthesized based on the 5'-end and 3'-end sequences of the structural gene indicated in the reference, to clone the region containing only the open reading frame of formate dehydrogenase. PCR was conduced by using plasmid (pMcFDH(E-P)) as a template with 30 cycles (at 95° C. for 45 seconds, at 50° C. for 1 minute, at 75° C. for 7 minutes) to obtain specifically amplified DNA. The resulting DNA fragment was double-digested with two restriction endonucleases of NcoI and XbaI. A plasmid vector pSE420D (JP-A 2000-189170) was double-digested with the NcoI and XbaI, and PCR amplified DNA fragment double-digested with the enzymes was ligated thereto with T4 DNA ligase; thus pSE-MCF15 was obtained. A map of plasmid is shown in FIG. 1 (PSE-MCF15). Nucleotide sequence analysis of the inserted DNA fragment revealed that the sequence encoding the protein agreed with the DNA sequence described in the reference. The determined formate dehydrogenase nucleotide sequence is shown in McFDH-ORF (SEQ ID NO:1), and the amino acid sequence of protein encoded by the gene is shown in McFDH-ORF-p (SEQ ID NO:2).

Figure 2:
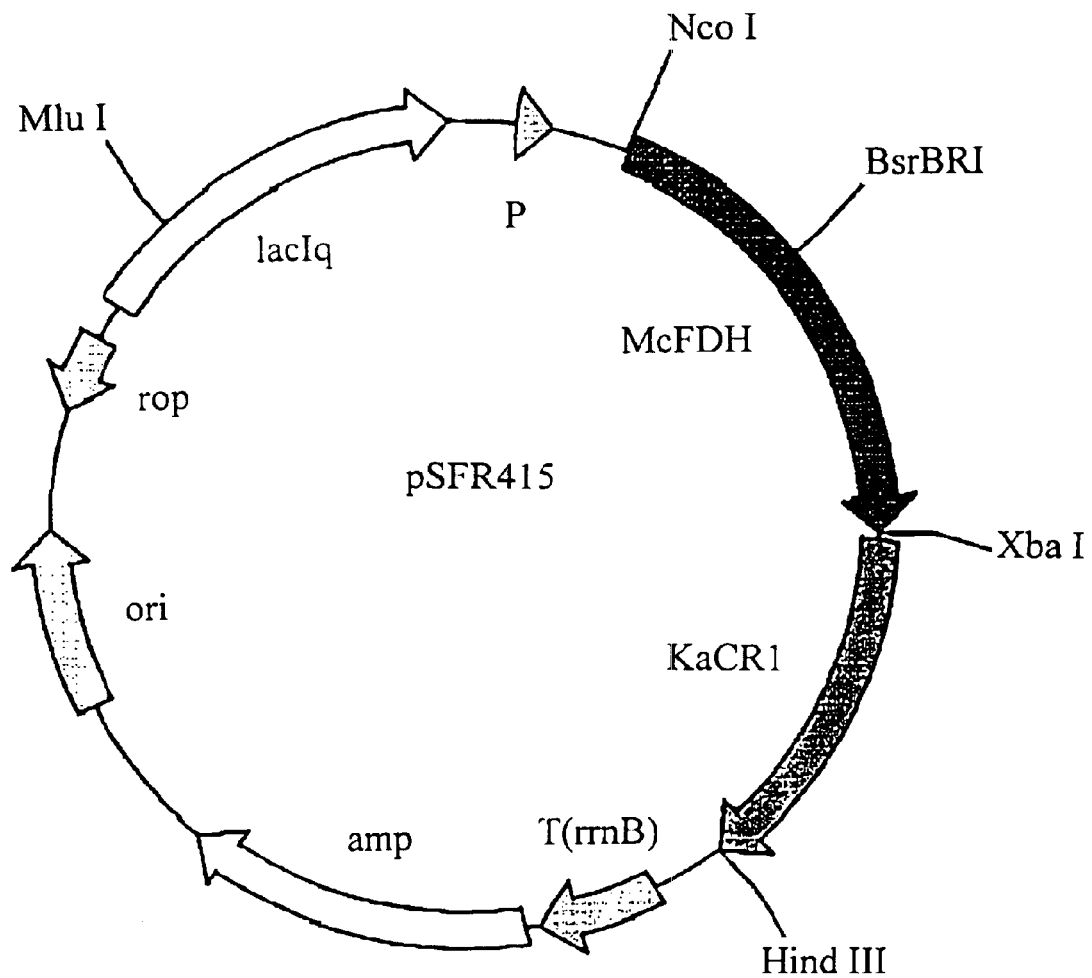
FIG. 2 shows the structure of plasmid pSFR415.

EXAMPLE 2
Construction of Coexpression Vector pSFR415 for *Mycobacterium vaccae*-derived Formate Dehydrogenase and *Kluyveromyces aestuarii*-derived Carbonyl Reductase To clone the region containing only the open reading frame of *Kluyveromyces aestuarii*-derived carbonyl reductase by PCR, primers KAR-BSG5-3 (5'-TAATCTAGAGGAATTCAATAATGGATCCAACAATGACGTTTC-3'/SEQ ID NO:5) and KAR-BSG3 (5'-TAGAAGCTTAAGCTATTAAACGCAAGTGTACCCAC-3'/SEQ ID NO:6) were synthesized. PCR was conduced by using pSE-KAR1 (JP-A 2000-236883) as a template with 30 cycles (at 95° C. for 30 seconds, at 50° C. for 1 minute, at 75° C. for 5 minutes) to obtain specifically amplified DNA. The resulting DNA fragment was double-digested with two restriction endonucleases of XbaI and HindIII. The plasmid pSE-MCF15 containing *Mycobacterium vaccae*-derived formate dehydrogenase constructed in Example 1 was double-digested with two restriction endonucleases of XbaI and HindIII, and the PCR-amplified DNA fragment double-digested with the enzymes was ligated thereto with T4 DNA ligase; thus plasmid pSFR415, which is capable of coexpressing formate dehydrogenase and carbonyl reductase, was obtained. A map of the plasmid pSFR415 is shown in FIG. 2. *E. coli* (JM109(pSFR415)) containing the plasmid has been deposited as follows.

Name and Address of Depositary Authority
Name: Patent and Bio-Resourse Center, National Institute of Advanced Industrial Science and Technology (AIST)
(Previous Name: National Institute of Bioscience and Human-Technology, Agency of Industrial Science and Technology)
Address: AIST Tsukuba Central 6, 1-1-3 Higashi, Tsukuba, Ibaraki, Japan (ZIP CODE: 305-8566)
Date of Deposition (Date of Original Deposition): Nov. 10, 2000
Accession Number: FERM BP-7391

EXAMPLE 3
Introduction of Mutations into *Mycobacterium vaccae*-derived Formate Dehydrogenase by PCR A primer MCF-ATG3 (5'-CTTTCTAGAGGAATTCAACCATGGCAAAAGTTCTGTCTGTTC-3'/SEQ ID NO:7) to substitute Ser for Cys at position 6 in *Mycobacterium vaccae*-derived formate dehydrogenase, and primers McFDH-7mut01 (5'-GTATCCGGTTTGCGACGTCGTGACGCTGAACTCCCCGCTGCACCCCGAA-3'/SEQ ID NO:8) and McFDH-7mut02 (5'-TTCGGGGTGCAGCGGGGAGTTCAGCGTCACGACGTCGCAAACCGGATAC-3'/SEQ ID NO:9) to substitute Ser for Cys at position 256 in *Mycobacterium vaccae*-derived formate dehydrogenase were synthesized based on the coexpression vector pSFR415 for *Mycobacterium vaccae*-derived formate dehydrogenase and *Kluyveromyces aestuarii*-derived carbonyl reductase, which had been constructed in Example 2. Hereinafter the substitution of Cys with Ser at position 6 is referred to as "C6S." According to this rule, the substitution of Cys with Ser at position 256 is referred to as "C256S."

The first-round PCR (at 94° C., for 30 seconds, at 50° C. for 30 seconds, at 72° C. for 30 seconds, 25 cycles) was carried out by using plasmid pSFR415 as a template and a set of primers MCF-ATG3 and McFDH-7mut02 as well as a set of primers McFDH-7mut01 and MCF-TAA3. Subsequently, the DNA fragment amplified by the first-round PCR was diluted and mixed, and primers MCF-ATG3 (SEQ ID NO:7) and MCF-TAA3 (SEQ ID NO:4) were added thereto. Then, the second-round PCR (at 94° C. for 30 seconds, at 50° C. for 30 seconds, at 72° C. for 30 seconds, 25 cycles) was performed. The resulting PCR-amplified fragment was double-digested with two restriction endonucleases of NcoI and XbaI. pSFR415 was double-digested with two restriction endonucleases of NcoI and XbaI, and the PCR-amplified fragment digested with the same enzymes was ligated thereto with T4 DNA ligase. Thus a plasmid pSFR411 was obtained, which is capable of coexpressing formate dehydrogenase, into which mutations C6S and C256S had been introduced, and carbonyl reductase. Nucleotide sequence analysis of the resulting plasmid was carried out to verify that it contains the desired mutations.

EXAMPLE 4
Construction of *Mycobacterium vaccae*-derived Formate Dehydrogenase Having C6S, C146S, and C256S Mutations Primers McFDH-12F (5'-CGGAAGTCACCTACTCAAACTCGATCAGCGTCG-3'/SEQ ID NO:10) and McFDH-12R (5'-

CGACGCTGATCGAGTTTGAGTAGGTGACTTCCG-3'/ SEQ ID NO:11) were synthesized to substitute Ser for Cys at position 146 in *Mycobacterium vaccae*-derived formate dehydrogenase, based on plasmid pSFR411 obtained in Example 3.

The first-round PCR (at 94° C. for 30 seconds, at 50° C. for 30 seconds, 72° C. for 30 seconds, 25 cycles) was carried out by using plasmid pSFR411 as a template and a set of primers MCF-ATG3 (SEQ ID NO:7) and McFDH-12R (SEQ ID NO:11) as well as a set of primers McFDH-12F (SEQ ID NO:10) and MCF-TAA3 (SEQ ID NO:4). Subsequently, the DNA fragment amplified by the first-round PCR was diluted and mixed, and primers MCF-ATG3 (SEQ ID NO:7) and MCF-TAA3 (SEQ ID NO:4) were added thereto. Then, the second-round PCR (at 94° C. for 30 seconds, at 50° C. for 30 seconds, at 72° C. for 30 seconds, 25 cycles) was performed. The resulting amplified PCR fragment was double-digested with two restriction endonucleases of NcoI and XbaI. pSFR411 was double-digested with two restriction endonucleases of NcoI and XbaI, and the PCR amplified fragment digested with the same enzymes was ligated thereto with T4 DNA ligase. Thus a plasmid pSFR412 was obtained, which is capable of coexpressing formate dehydrogenase into which mutations C6S, C146S, and C256S had been introduced, and carbonyl reductase. Nucleotide sequence analysis of the resulting plasmid was carried out to verify that it contains the desired mutations.

EXAMPLE 5

Construction of *Mycobacterium vaccae*-derived Formate Dehydrogenase Having C6S, C249S, and C256S Mutations Primers McFDH-13F (5'-GACATGTATCCGGTTTCTGACGTCGTGACGCTG-3'/ SEQ ID NO:12) and McFDH-13R (5'-CAGCGTCACGACGTCAGAAACCGGATACATGTC-3'/ SEQ ID NO:13) were synthesized to substitute Ser for Cys at position 249 in *Mycobacterium vaccae*-derived formate dehydrogenase, based on plasmid pSFR411 obtained in Example 3.

The first-round PCR (at 94° C. for 30 seconds, at 50° C. for 30 seconds, 72° C. for 30 seconds, 25 cycles) was carried out by using plasmid pSFR411 as a template and a set of primers MCF-ATG3 (SEQ ID NO:7) and McFDH-13R (SEQ ID NO:13) as well as a set of primers McFDH-13F (SEQ ID NO:12) and MCF-TAA3 (SEQ ID NO:4). Subsequently, the DNA fragment amplified by the first-round PCR was diluted and mixed, and primers MCF-ATG3 (SEQ ID NO:7) and MCF-TAA3 (SEQ ID NO:4) were added thereto. Then, the second-round PCR (at 94° C. for 30 seconds, at 50° C. for 30 seconds, at 72° C. for 30 seconds, 25 cycles) was performed. The resulting amplified PCR fragment was double-digested with two restriction endonucleases of NcoI and XbaI. pSFR411 was double-digested with two restriction endonucleases of NcoI and XbaI, and the PCR-amplified fragment digested with the same enzymes was ligated thereto with T4 DNA ligase. Thus a plasmid pSFR413 was obtained, which is capable of coexpressing formate dehydrogenase into which mutations C6S, C249S, and C256S had been introduced, and carbonyl reductase. Nucleotide sequence analysis of the resulting plasmid was carried out to verify that it contains the desired mutations.

EXAMPLE 6

Construction of *Mycobacterium vaccae*-derived Formate Dehydrogenase Having C6S, C256S, and C355S Mutations Primers McFDH-14F (5'-CGAGATCCTGGAGTCATTCTTCGAAGGCCGTCCGA-3'/SEQ ID NO:14) and McFDH-14R (5'-TCGGACGGCCTTCGAAGAATGACTCCAGGATCTCG-3'/SEQ ID NO:15) were synthesized to substitute Ser for Cys at position 355 in *Mycobacterium vaccae*-derived formate dehydrogenase, based on the obtained plasmid pSFR411.

The first-round PCR (at 94° C. for 30 seconds, at 50° C. for 30 seconds, 72° C. for 30 seconds, 25 cycles) was carried out by using plasmid pSFR411 as a template and a set of primers MCF-ATG3 (SEQ ID NO:7) and McFDH-14R (SEQ ID NO:15) as well as a set of primers McFDH-14F (SEQ ID NO:14) and MCF-TAA3 (SEQ ID NO:4). Subsequently, the DNA fragment amplified by the first-round PCR was diluted and mixed, and primers MCF-ATG3 (SEQ ID NO:7) and MCF-TAA3 (SEQ ID NO:4) were added thereto. Then, the second-round PCR (at 94° C. for 30 seconds, at 50° C. for 30 seconds, at 72° C. for 30 seconds, 25 cycles) was performed. The resulting amplified PCR fragment was double-digested with two restriction endonucleases of NcoI and XbaI. pSFR411 was double-digested with two restriction endonucleases of NcoI and XbaI, and the PCR-amplified fragment digested with the same enzymes was ligated thereto with T4 DNA ligase. Thus a plasmid pSFR414 was obtained, which is capable of coexpressing formate dehydrogenase, into which mutations C6S, C256S, and C355S had been introduced, and carbonyl reductase. Nucleotide sequence analysis of the resulting plasmid was carried out to verify that it contains the desired mutations.

EXAMPLE 7

Construction of *Mycobacterium vaccae*-derived Formate Dehydrogenase Having C6A and C256S Mutations Primers MCF-416F (5'-ATGGCAAAAGTTTTAGCTGTTCTTTACGAT-3'/SEQ ID NO:16) and MCF-416R (5'-ATCGTAAAGAACAGCTAAAACTTTTGCCAT-3'/SEQ ID NO:17) to substitute a residue at position 6 with Ala in *Mycobacterium vaccae*-derived formate dehydrogenase as well as primers, 170F (5'-GGCAAATATTCTGAAATGAGC-3'/SEQ ID NO:18) and MCF-777R (5'-TCACGACGTCGCAAACCGGA-3'/SEQ ID NO:19), were synthesized based on plasmid pSFR411 obtained in Example 3.

The first-round PCR (at 94° C. for 30 seconds, at 50° C. for 30 seconds, 72° C. for 30 seconds, 25 cycles) was carried out by using plasmid pSFR411 as a template and a set of primers 170F (SEQ ID NO:18) and MCF-416R (SEQ ID NO:17) as well as a set of primers MCF-416F (SEQ ID NO:16) and MCF-777R (SEQ ID NO:19). Subsequently, the DNA fragment amplified by the first-round PCR was diluted and mixed, and primers 170F (SEQ ID NO:18) and MCF-777R (SEQ ID NO:19) were added thereto. Then, the second-round PCR (at 94° C. for 30 seconds, at 50° C. for 30 seconds, at 72° C. for 30 seconds, 25 cycles) was performed.

The resulting amplified PCR fragment was double-digested with two restriction endonucleases of NheI and BglII. pSFR411 was double-digested with two restriction endonucleases of NheI and BglII, and the PCR-amplified fragment digested with the same enzymes was ligated thereto with T4 DNA ligase. Thus a plasmid pSFR416 was obtained, which is capable of coexpressing formate dehydrogenase, into which mutations C6A and C256S had been introduced, and carbonyl reductase. Nucleotide sequence analysis of the resulting plasmid was carried out to verify that it contains the desired mutations.

EXAMPLE 8

Construction of *Mycobacterium vaccae*-derived Formate Dehydrogenase Having C6V and C256S Mutations Primers MCF-417F (5'-ATGGCAAAAGTTTTAGTAGTTCTTTACGAT-3'/SEQ ID NO:20) and MCF-417R (5'-ATCGTAAAGAACTACTAAAACTTTTGCCAT-3'/SEQ ID NO:21) were synthesized to substitute a residue at position 6 with Val in *Mycobacterium vaccae*-derived formate dehydrogenase, based on plasmid pSFR411 obtained in Example 3.

The first-round PCR (at 94° C. for 30 seconds, at 50° C. for 30 seconds, 72° C. for 30 seconds, 25 cycles) was carried out by using plasmid pSFR411 as a template and a set of primers 170F (SEQ ID NO:18) and MCF-417R (SEQ ID NO:21) as well as a set of primers MCF-417F (SEQ ID NO:20) and MCF-777R (SEQ ID NO:19). Subsequently, the DNA fragment amplified by the first-round PCR was diluted and mixed, and primers 170F (SEQ ID NO:18) and MCF-777R (SEQ ID NO:19) were added thereto. Then, the second-round PCR (at 94° C. for 30 seconds, at 50° C. for 30 seconds, at 72° C. for 30 seconds, 25 cycles) was performed.

The resulting amplified PCR fragment was double-digested with two restriction endonucleases of NheI and BglII. pSFR411 was double-digested with two restriction endonucleases of NheI and BglII, and the PCR-amplified fragment digested with the same enzymes was ligated thereto with T4 DNA ligase. Thus a plasmid pSFR417 was obtained, which is capable of coexpressing formnate dehydrogenase, into which mutations C6V and C256S had been introduced, and carbonyl reductase. Nucleotide sequence analysis of the resulting plasmid was carried out to verify that it contains the desired mutations.

EXAMPLE 9
Construction of *Mycobacterium vaccae*-derived Formate Dehydrogenase Having C6S and C256A Mutations Primers MCF-418F (5'-GTGACGCTGAACGCTCCGCTGCACCCC-3'/SEQ ID NO:22) and MCF-418R (5'-GGGGTGCAGCGGAGCGTTCAGCGTCAC-3'/SEQ ID NO:23) were synthesized to substitute a residue at position 256 with Ala in *Mycobacterium vaccae*-derived formate dehydrogenase, based on plasmid pSFR411 obtained in Example 3.

The first-round PCR (at 94° C. for 30 seconds, at 50° C. for 30 seconds, 72° C. for 30 seconds, 25 cycles) was carried out by using plasmid pSFR411 as a template and a set of primers MCF-ATG3 (SEQ ID NO:7) and MCF-418R (SEQ ID NO:23) as well as a set of primers MCF-418F (SEQ ID NO:22) and MCF-TAA3 (SEQ ID NO:4). Subsequently, the DNA fragment amplified by the first-round PCR was diluted and mixed, and primers MCF-ATG3 (SEQ ID NO:7) and MCF-TAA3 (SEQ ID NO:4) were added thereto. Then, the second-round PCR (at 94° C. for 30 seconds, at 50° C. for 30 seconds, at 72° C. for 30 seconds, 25 cycles) was performed.

The resulting amplified PCR fragment was double-digested with two restriction endonucleases of BglII and XbaI. pSFR411 was double-digested with two restriction endonucleases of BglII and Xbal, and the PCR-amplified fragment digested with the same enzymes was ligated thereto with T4 DNA ligase. Thus a plasmid pSFR418 was obtained, which is capable of coexpressing formate dehydrogenase, into which mutations C6S and C256A had been introduced, and carbonyl reductase. Nucleotide sequence analysis of the resulting plasmid was carried out to verify that it contains the desired mutations.

EXAMPLE 10
Construction of *Mycobacterium vaccae*-derived Formate Dehydrogenase Having C6S and C256V Mutations Primers MCF-419F (5'-GTGACGCTGAACGTTCCGCTGCACCCC-3'/SEQ ID NO:24) and MCF-419R (5'-GGGGTGCAGCGGAACGTTCAGCGTCAC-3'/SEQ ID NO:25) were synthesized to substitute a residue at position 256 with Val in *Mycobacterium vaccae*-derived formate dehydrogenase, based on plasmid pSFR411 obtained in Example 3.

The first-round PCR (at 94° C. for 30 seconds, at 50° C. for 30 seconds, 72° C. for 30 seconds, 25 cycles) was carried out by using plasmid pSFR411 as a template and a set of primers MCF-ATG3 (SEQ ID NO:7) and MCF-418R (SEQ ID NO:23) as well as a set of primers MCF-418F (SEQ ID NO:22) and MCF-TAA3 (SEQ ID NO:4). Subsequently, the DNA fragment amplified by the first-round PCR was diluted and mixed, and primers MCF-ATG3 (SEQ ID NO:7) and MCF-TAA3 (SEQ ID NO:4) were added thereto. Then, the second-round PCR (at 94° C. for 30 seconds, at 50° C. for 30 seconds, at 72° C. for 30 seconds, 25 cycles) was performed. The resulting amplified PCR fragment was double-digested with two restriction endonucleases of BglII and XbaI. pSFR411 was double-digested with two restriction endonucleases of BglII and XbaI, and the PCR-amplified fragment digested with the same enzymes was ligated thereto with T4 DNA ligase. Thus a plasmid pSFR419 was obtained, which is capable of coexpressing formate dehydrogenase, into which mutations C6S and C256V had been introduced, and carbonyl reductase. Nucleotide sequence analysis of the resulting plasmid was carried out to verify that it contains the desired mutations.

EXAMPLE 11
Construction of *Mycobacterium vaccae*-derived Formate Dehydrogenase Having C146S Mutation After pSFR415 constructed in Example 2 was digested with two restriction endonucleases of BglII and BsrBRI, and precipitated with ethanol, it was subjected to agarose electrophoresis. A band of about 6 kbp was cut out, and DNA contained in the band was purified and recovered by using Sephaglas BandPrep (Amersham Pharmacia Biotech). After pSFR412 constructed in Example 4 was digested with two restriction endonucleases of BglII and BsrBRI, and precipitated with ethanol, it was subjected to agarose electrophoresis. A band of about 0.4 kbp was cut out, and DNA contained in the band was purified and recovered by using Sephaglas BandPrep (Amersham Pharmacia Biotech). Both DNA fragments were combined together (equal molar amount), and then they were ligated to each other with T4 DNA ligase. Thus a plasmid pSFR420 was obtained, which is capable of coexpressing formate dehydrogenase, into which mutation C146S had been introduced, and carbonyl reductase. Nucleotide sequence analysis of the resulting plasmid was carried out to verify that it contains the desired mutations.

EXAMPLE 12
Construction of *Mycobacterium vaccae*-derived Formate Dehydrogenase Having C256S Mutation After pSFR415 constructed in Example 2 was digested with two restriction endonucleases of MluI and BsrBRI, and precipitated with ethanol, it was subjected to agarose electrophoresis. A band of about 1.5 kbp was cut out, and DNA contained in the band was purified and recovered by using Sephaglas BandPrep (Amersham Pharmacia Biotech). After pSFR412 constructed in Example 4 was digested with two restriction endonucleases of MluI and BsrBRI, and precipitated with ethanol, it was subjected to agarose electrophoresis. A band of about 4.8 kbp was cut out, and DNA contained in the band was purified and recovered by using Sephaglas BandPrep (Amersham Pharmacia Biotech). Both DNA fragments were combined together (equal molar amount), and then they were ligated to each other with T4 DNA ligase. Thus a plasmid pSFR421 was obtained, which is capable of coexpressing formate dehydrogenase, into which mutation C256S had been introduced, and carbonyl reductase. Nucleotide sequence analysis of the resulting plasmid was carried out to verify that it contains the desired mutations.

EXAMPLE 13
Construction of *Mycobacterium vaccae*-derived Formate Dehydrogenase Having C146S and C256S Mutations After pSFR415 constructed in Example 2 was digested with two restriction endonucleases of MluI and BglII, and precipitated with ethanol, it was subjected to agarose electrophoresis. A band of about 1.3 kbp was cut out, and DNA contained in the band was purified and recovered by using Sephaglas BandPrep (Amersham Pharmacia Biotech). After pSFR412 constructed in Example 4 was digested with two restriction endonucleases of MluI and BglII, and precipitated with ethanol, it was subjected to agarose electrophoresis. A band of about 5.1 kbp was cut out, and DNA contained in the band was purified and recovered by using Sephaglas BandPrep (Amersham Pharmacia Biotech). Both DNA fragments were combined together (equal molar amount), and then they were ligated to each other with T4 DNA ligase. Thus a plasmid pSFR422 was obtained, which is capable of coexpressing formate dehydrogenase, into which mutations C146S and C256S had been introduced, and carbonyl reductase. Nucleotide sequence analysis of the resulting plasmid was carried out to verify that it contains the desired mutations.

EXAMPLE 14
Construction of *Mycobacterium vaccae*-derived Formate Dehydrogenase Having C256V Mutation After pSFR415 constructed in Example 2 was digested with two restriction endonucleases of MluI and BglII, and precipitated with ethanol, it was subjected to agarose electrophoresis. A band of about 1.3 kbp was cut out, and DNA contained in the band was purified and recovered by using Sephaglas BandPrep (Amersham Pharmacia Biotech). After pSFR419 constructed in Example 10 was digested with two restriction endonucleases of MluI and BglII, and precipitated with ethanol, it was subjected to agarose electrophoresis. A band of about 5.1 kbp was cut out, and DNA contained in the band was purified and recovered by using Sephaglas BandPrep (Amersham Pharmacia Biotech). Both DNA fragments were combined together (equal molar amount), and then they were ligated to each other with T4 DNA ligase. Thus a plasmid pSFR423 was obtained, which is capable of coexpressing formate dehydrogenase, into which mutation C256V had been introduced, and carbonyl reductase. Nucleotide sequence analysis of the resulting plasmid was carried out to verify that it contains the desired mutations.

EXAMPLE 15
Construction of *Mycobacterium vaccae*-derived Formate Dehydrogenase Having C146S and C256V Mutations After pSFR415 constructed in Example 2 was digested with two restriction endonucleases of MluI and BglII, and precipitated with ethanol, it was subjected to agarose electrophoresis. A band of about 1.3 kbp was cut out, and DNA contained in the band was purified and recovered by using Sephaglas BandPrep (Amersham Pharmacia Biotech). After pSFR412 constructed in Example 4 was digested with two restriction endonucleases of BglII and BsrBRI, and precipitated with ethanol, it was subjected to agarose electrophoresis. A band of about 0.4 kbp was cut out, and DNA contained in the band was purified and recovered by using Sephaglas BandPrep (Amersham Pharmacia Biotech). After pSFR419 constructed in Example 10 was digested with two restriction endonucleases of MluI and BsrBRI, and precipitated with ethanol, it was subjected to agarose electrophoresis. A band of about 4.7 kbp was cut out, and DNA contained in the band was purified and recovered by using Sephaglas BandPrep (Amersham Pharmacia Biotech). Both DNA fragments were combined together (equal molar amount), and then they were ligated to each other with T4 DNA ligase. Thus a plasmid pSFR424 was obtained, which is capable of coexpressing formate dehydrogenase, into which mutations C146S and C256V had been introduced, and carbonyl reductase. Nucleotide sequence analysis of the resulting plasmid was carried out to verify that it contains the desired mutations.

EXAMPLE 16
Construction of *Mycobacterium vaccae*-derived Formate Dehydrogenase Having C6A and C256V Mutations After pSFR416 constructed in Example 7 was digested with two restriction endonucleases of MluI and BglII, and precipitated with ethanol, it was subjected to agarose electrophoresis. A band of about 1.3 kbp was cut out, and DNA contained in the band was purified and recovered by using Sephaglas BandPrep (Amersham Pharmacia Biotech). After pSFR419 constructed in Example 10 was digested with two restriction endonucleases of MluI and BglII, and precipitated with ethanol, it was subjected to agarose electrophoresis. A band of about 5.1 kbp was cut out, and DNA contained in the band was purified and recovered by using Sephaglas BandPrep (Amersham Pharmacia Biotech). Both DNA fragments were combined together (equal molar amount), and then they were ligated to each other with T4 DNA ligase. Thus a plasmid pSFR425 was obtained, which is capable of coexpressing formate dehydrogenase, into which mutations C6A and C256V had been introduced, and carbonyl reductase. Nucleotide sequence analysis of the resulting plasmid was carried out to verify that it contains the desired mutations.

EXAMPLE 17
Construction of *Mycobacterium vaccae*-derived Formate Dehydrogenase Having C6A, C146S, and C256V Mutations After pSFR416 constructed in Example 7 was digested with two restriction endonucleases of MluI and BglII, and precipitated with ethanol, it was subjected to agarose electrophoresis. A band of about 1.3 kbp was cut out, and DNA contained in the band was purified and recovered by using Sephaglas BandPrep (Amersham Pharmacia Biotech). After pSFR412 constructed in Example 4 was digested with two restriction endonucleases of BglII and BsrBRI, and precipitated with ethanol, it was subjected to agarose electrophoresis. A band of about 0.4 kbp was cut out, and DNA contained in the band was purified and recovered by using Sephaglas BandPrep (Amersham Pharmacia Biotech). After pSFR419 constructed in Example 10 was digested with two restriction endonucleases of MluI and BsrBRI, and precipitated with ethanol, it was subjected to agarose electrophoresis. A band of about 4.7 kbp was cut out, and DNA contained in the band was purified and recovered by using Sephaglas BandPrep (Amersham Pharmacia Biotech). Both DNA fragments were combined together (equal molar amount), and then they were ligated to each other with T4 DNA ligase. Thus a plasmid pSFR426 was obtained, which is capable of coexpressing formate dehydrogenase, into which mutation C6A, C146S, and C256V had been introduced, and carbonyl reductase. Nucleotide sequence analysis of the resulting plasmid was carried out to verify that it contains the desired mutations. E. coli (JM109(pSFR426)) containing the plasmid has been deposited as follows.

Name and Address of Depositary Authority
Name: Patent and Bio-Resourse Center, National Institute of Advanced Industrial Science and Technology (AIST)
(Previous Name: National Institute of Bioscience and Human-Technology, Agency of Industrial Science and Technology)
Address: AIST Tsukuba Central 6, 1-1-3 Higashi, Tsukuba, Ibaraki, Japan (ZIP CODE: 305–8566)
Date of Deposition (Date of Original Deposition): Nov. 10, 2000 Accession Number: FERM BP-7392

EXAMPLE 18
Construction of *Mycobacterium vaccae*-derived Formate Dehydrogenase Having C6A, C146A, and C256V Mutations Primers MCF-427F (SEQ ID NO:26) and MCF-427R (SEQ ID NO:27) were synthesized to substitute a residue at position 146 with Ala in *Mycobacterium vaccae*-derived formate dehydrogenase, based on plasmid pSFR426 obtained in Example 15.

```
MCF-427F
GAAGTCACCTACGCTAACTCGATCAGC   (SEQ ID NO:26)

MCF-427R
GCTGATCGAGTTAGCGTAGGTGACTTC   (SEQ ID NO:27)
```

The first-round PCR (at 94° C. for 30 seconds, at 50° C. for 30 seconds, 72° C. for 60 seconds, 25 cycles) was carried out by using plasmid pSFR426 as a template and a set of primers MCF-ATG3 (SEQ ID NO:7) and MCF-427R (SEQ ID NO:27) as well as a set of primers MCF-427F (SEQ ID NO:26) and MCF-TAA3 (SEQ ID NO:4). Subsequently, the DNA fragment amplified by the first-round PCR was diluted and mixed, and primers MCF-ATG3 (SEQ ID NO:7) and MCF-TAA3 (SEQ ID NO:4) were added thereto. Then, the second-round PCR (at 94° C. for 30 seconds, at 50° C. for 30 seconds, at 72° C. for 60 seconds, 25 cycles) was performed.

The resulting amplified PCR fragment was double-digested with two restriction endonucleases of BglII and XbaI.

pSFR426 was double-digested with two restriction endonucleases of BglII and XbaI, and the PCR-amplified fragment digested with the same enzymes was ligated thereto with T4 DNA ligase. Thus a plasmid pSFR427 was obtained, which is capable of coexpressing formate dehydrogenase, into which mutations C6A, C146A, and C256V had been introduced, and carbonyl reductase. Nucleotide sequence analysis of the resulting plasmid was carried out to verify that it contains the desired mutations.

EXAMPLE 19
Coexpression of *Mycobacterium vaccae*-derived Formate Dehydrogenase and *Kluyveromyces aestuarii*-derived Carbonyl Reductase in *E. coli*

*E. coli* W3 110 strain was transformed with each of plasmids co-expressing *Mycobacterium vaccae*-derived formate dehydrogenase and *Kluyveromyces aestuarii*-derived carbonyl reductase, which had been constructed in Examples 2 to 18. Each recombinant *E. coli* was inoculated into liquid culture medium (1% bacto-triptone, 0.5% bacto-yeast extract, 1.0% sodium chloride; hereinafter referred to as LB medium), and cultured at 30° C. overnight. Then isopropylthio-β-galactopyranoside (hereinafter referred to as IPTG) was added to the culture, and the cultivation was fuirther continued. The bacterial cells were harvested by centrifugal separation, and then the cells were suspended in 100 mM potassium phosphate buffer (pH 7.0) containing 0.02% 2-mercaptoethanol and 10 mM ethylenediaminetetraacetic acid disodium salt. The bacterial cells were disrupted by the treatment with an airtight sonication device UCD-200TM (Cosmo Bio) for 3 minutes. The bacterial cell lysate was separated by centrifugation, and the resulting supernatant was recovered as a bacterial cell extract. The formate dehydrogenase activity and activity of reducing ethyl 4-chloroacetoacetate were assayed. The quantity of protein was measured by a Bio-Rad Protein Assay Kit (Bio-Rad). Standard protein used was bovine plasma albumin. The enzyme activity in crude enzyme solution obtained from each recombinant *E. coli* is shown in Table 1.

TABLE 1

| Plasmid | 6-Cys | 146-Cys | 256-Cys | U/mg-protein FDH | ECAA-R |
|---|---|---|---|---|---|
| pSFR415 | Cys | Cys | [Cys] | 1.46 | 1.99 |
| pSFR412 | *Ser* | *Ser* | *Ser* | 0.127 | 2.15 |
| pSFR416 | #Ala# | Cys | *Ser* | 0.751 | 1.85 |
| pSFR417 | =Val= | Cys | *Ser* | 0.659 | 1.56 |
| pSFR418 | *Ser* | Cys | #Ala# | 0.193 | 1.35 |
| pSFR419 | *Ser* | Cys | =Val= | 0.258 | 1.18 |
| pSFR420 | Cys | *Ser* | [Cys] | 1.22 | 2.68 |
| pSFR421 | Cys | Cys | *Ser* | 1.40 | 2.61 |
| pSFR422 | Cys | *Ser* | *Ser* | 0.960 | 4.35 |
| pSFR423 | Cys | Cys | =Val= | 1.47 | 2.08 |
| pSFR424 | Cys | *Ser* | =Val= | 0.967 | 2.13 |
| pSFR425 | #Ala# | Cys | =Val= | 1.16 | 2.05 |
| pSFR426 | #Ala# | *Ser* | =Val= | 0.716 | 1.66 |
| pSFR427 | #Ala# | #Ala# | =Val= | 0.311 | 1.51 |

ECAA-R represents activity of *Kluyveromyces aestuarii*-derived carbonyl reductase;
FDH represents formate dehydrogenase activity.

EXAMPLE 20
Assay for resistance of *Mycobacterium vaccae*-derived Formate Dehydrogenase to ethyl 4-chloroacetoacetate Assay for the resistance of formate dehydrogenase to ethyl 4-chloroacetoacetate was conducted by incubating, at 25° C. for 20 minutes, a solution containing 10 mU of formate dehydrogenase of each recombinant bacterium obtained in Example 19, 20 μmol of ethyl 4-chloroacetoacetate, 100 mM potassium phosphate buffer (pH 7.0), and bovine albumin (Fraction V; Sigma), which was contained in the solution so that the total protein quantity should be 100 μg, and then adding 2.5 μmol of $NAD^+$ and 100 μmol of sodium formate thereto to measure the change in absorbance at 340 nm. A control experiment was conducted by the incubation under the condition without ethyl 4-chloroacetoacetate at 25° C. for 20 minutes and then adding 20 μmol of ethyl 4-chloroacetoacetate, 2.5 μmol of $NAD^+$, and 100 μmol of sodium formate thereto to measure the change in absorbance at 340 nm.

Formate dehydrogenase activity in an enzyme solution prepared from each recombinant *E coli* is shown in Table 2. The residual activity after the treatment for 20 minutes is indicated in the column of ratio. Substitution of Cys with Ser, Ala, or Val at position 256 gave the resistance to ethyl 4-chloroacetoacetate.

TABLE 2

| Plasmid  | 6-Cys | 146-Cys | 256-Cys | ratio   |
|----------|-------|---------|---------|---------|
| pSFR415  | Cys   | Cys     | [Cys]   | [7.43%] |
| pSFR412  | *Ser* | *Ser*   | *Ser*   | 116%    |
| pSFR416  | #Ala# | Cys     | *Ser*   | 97.4%   |
| pSFR417  | =Val= | Cys     | *Ser*   | 92.1%   |
| pSFR418  | *Ser* | Cys     | #Ala#   | 120%    |
| pSFR419  | *Ser* | Cys     | =Val=   | 94.0%   |
| pSFR420  | Cys   | *Ser*   | [Cys]   | [7.67%] |
| pSFR421  | Cys   | Cys     | *Ser*   | 99.3%   |
| pSFR422  | Cys   | *Ser*   | *Ser*   | 118%    |
| pSFR423  | Cys   | Cys     | =Val=   | 100%    |
| pSFR424  | Cys   | *Ser*   | =Val=   | 104%    |
| pSFR425  | #Ala# | Cys     | =Val=   | 94.5%   |
| pSFR426  | #Ala# | *Ser*   | =Val=   | 108%    |
| pSFR427  | #Ala# | #Ala#   | =Val=   | 106%    |

EXAMPLE 21
Measurement of activation of *Mycobacterium vaccae*-derived Formate Dehydrogenase by Ethyl Acetate The activation of formate dehydrogenase by ethyl acetate was tested by measuring the activity of formate dehydrogenase obtained in Example 19 under a condition in the presence of 5% ethyl acetate.

The enzyme activity in the enzyme solution obtained form each recombinant *E. coli* in the presence of ethyl acetate is shown in Table 3. The substitution of Cys with Ser or Ala at position 146 gave the activation effect of ethyl acetate.

TABLE 3

| Plasmid  | 6-Cys | 146-Cys | 256-Cys | ratio   |
|----------|-------|---------|---------|---------|
| pSFR415  | Cys   | Cys     | [Cys]   | 121%    |
| pSFR412  | *Ser* | *Ser*   | *Ser*   | [225%]  |
| pSFR416  | #Ala# | Cys     | *Ser*   | 109%    |
| pSFR417  | =Val= | Cys     | *Ser*   | 105%    |
| pSFR418  | *Ser* | Cys     | #Ala#   | 125%    |
| pSFR419  | *Ser* | Cys     | =Val=   | 110%    |
| pSFR420  | Cys   | *Ser*   | [Cys]   | [181%]  |
| pSFR421  | Cys   | Cys     | *Ser*   | 125%    |
| pSFR422  | Cys   | *Ser*   | *Ser*   | [224%]  |
| pSFR423  | Cys   | Cys     | =Val=   | 111%    |
| pSFR424  | Cys   | *Ser*   | =Val=   | [185%]  |
| pSFR425  | #Ala# | Cys     | =Val=   | 111%    |
| pSFR426  | #Ala# | *Ser*   | =Val=   | [208%]  |
| pSFR427  | #Ala# | #Ala#   | =Val=   | [219%]  |

EXAMPLE 22
Synthesis of Ethyl (S)-4-chloro-3-hydroxybutyrate by Recombinant *E. coli*

*E. coli* W3110 strain was transformed with each of plasmids co-expressing *Mycobacterium vaccae*-derived formate dehydrogenase and *Kluyveromyces aestuarii*-derived carbonyl reductase, which had been constructed in Examples 2 to 18. Each recombinant *E. coli* was inoculated into liquid LB medium and cultured at 30° C. overnight. Then the *E. coli* was inoculated into a culture medium (2% bacto-triptone, 1% bacto-yeast extract, 1.0% sodium chloride, pH 7.2) and cultured at 30° C. overnight. After IPTG was added, the cultivation was further continued. The resulting *E. coli* cells were harvested. The reduction of ethyl 4-chloroacetoacetate was performed by using them.

20 mL of reaction solution containing each *E. coli* cells prepared from 20 mL of the culture, 500 mM potassium phosphate buffer (pH 6.3), 3% ethyl 4-chloroacetoacetate, and 365 mM sodium formate was incubated at 20° C. overnight while being stirred. The generated ethyl 4-chloro-3-hydroxybutyrate was quantitated by gas chromatography using a 3.2 mm×2.1 m glass column filled with 5% liquid Thermon 3000, carrier Chromosorb W (60–80 mesh) AW-DMCS (Thermon 3000 5% chromosorb W60–80 (AW-DMCS), Shinwa Chemical Industries, Ltd.) and using flame ionization detector (FID) at a column temperature of 150° C. The quantity of ethyl (S)-4-chloro-3-hydroxybutyrate generated by each recombinant *E. coli* is indicated in Table 4. The substitution of Cys with Ser, Ala, or Val at position 6, Cys with Ser or Ala at position 146, and Cys with Ser, Ala, or Val at position 256, enhanced the efficiency of conversion.

TABLE 4

| Plasmid  | 6-Cys | 146-Cys | 256-Cys | g/L  |
|----------|-------|---------|---------|------|
| pSFR415  | Cys   | Cys     | [Cys]   | 17.5 |
| pSFR412  | *Ser* | *Ser*   | *Ser*   | 24.5 |
| pSFR416  | #Ala# | Cys     | *Ser*   | 25.8 |
| pSFR417  | =Val= | Cys     | *Ser*   | 25.2 |
| pSFR418  | *Ser* | Cys     | #Ala#   | 22.4 |
| pSFR419  | *Ser* | Cys     | =Val=   | 25.5 |
| pSFR420  | Cys   | *Ser*   | [Cys]   | 19.1 |
| pSFR421  | Cys   | Cys     | *Ser*   | 30.5 |
| pSFR422  | Cys   | *Ser*   | *Ser*   | 25.5 |
| pSFR423  | Cys   | Cys     | =Val=   | 30.6 |
| pSFR424  | Cys   | *Ser*   | =Val=   | 31.0 |
| pSFR425  | #Ala# | Cys     | =Val=   | 29.6 |
| pSFR426  | #Ala# | *Ser*   | =Val=   | 32.2 |
| pSFR427  | #Ala# | #Ala#   | =Val=   | 27.7 |

What is claimed is:

1. An isolated polypeptide comprising a variant of the amino acid sequence of SEQ ID NO: 2, wherein the residue at position 146 of SEQ ID NO: 2 is an amino acid other than cysteine while the remaining residues are left unchanged, and wherein the polypeptide has increased formate dehydrogenase activity in the presence of an organic solvent in comparison to the protein consisting of the amino acid sequence of SEQ ID NO: 2.

2. The polypeptide of claim 1, wherein the residue at position 146 is serine.

3. The polypeptide of claim 1, wherein the residue at position 146 is alanine.

4. An isolated polypeptide comprising a variant of the amino acid sequence of SEQ ID NO: 2, wherein the residues at positions 146 and 256 of SEQ ID NO: 2 are amino acids other than cysteine while the remaining residues are left unchanged, and wherein the polypeptide has increased formate dehydrogenase activity in the presence of an organic solvent in comparison to the protein consisting of the amino acid sequence of SEQ ID NO: 2.

5. The polypeptide of claim 4, wherein the residue at position 146 is serine or valine and the residue at position 256 is serine, alanine, or valine.

6. The polypeptide of claim 4, wherein the residue at position 146 is serine and the residue at position 256 is serine.

7. The polypeptide of claim 4, wherein the residue at position 146 is serine and the residue at position 256 is valine.

8. A method for producing a reduced form of β-nicotinamide adenine dinucleotide from an oxidized form of β-nicotinamide adenine dinucleotide, said method comprising contacting the polypeptide of claim 1 with the oxidized form of β-nicotinamide adenine dinucleotide.

9. A method for producing a reduced form of β-nicotinamide adenine dinucleotide from an oxidized form of β-nicotinamide adenine dinucleotide, said method comprising contacting the polypeptide of claim 4 with the oxidized form of β-nicotinamide adenine dinucleotide.

10. A method for producing a reduced product from an oxidized substrate, said method comprising the steps of:

(1) producing a reduced form of β-nicotinamide adenine dinucleotide by the method of claim 8; and (2) contacting the reduced form of β-nicotinamide adenine dinucleotide of step (1) and an oxidized substrate with a reductase that produces the reduced product from the oxidized substrate in the presence of the reduced form of β-nicotinamide adenine dinucleotide, thereby producing the reduced product.

11. A method for producing a reduced product from an oxidized substrate, said method comprising the steps of:

(1) producing a reduced form of β-nicotinamide adenine dinucleotide by the method of claim 9; and (2) contacting the reduced form of β-nicotinamide adenine dinucleotide of step (1) and an oxidized substrate with a reductase that produces the reduced product from the oxidized substrate in the presence of the reduced form of β-nicotinamide adenine dinucleotide, thereby producing the reduced product.

12. The method of claim 10, wherein said oxidized substrate is a ketone and said reduced product is an alcohol.

13. The method of claim 11, wherein said oxidized substrate is a ketone and said reduced product is an alcohol.

14. The method of claim 12, wherein said ketone is 4-haloacetoacetate ester and said alcohol is (S)-4-halo-3-hydroxybutyrate ester.

15. The method of claim 13, wherein said ketone is 4-haloacetoacetate ester and said alcohol is (S)-4-halo-3-hydroxybutyrate ester.

16. The method of claim 10, wherein said reductase is *Kluyveromyces aestuarii*-derived carbonyl reductase.

17. The method of claim 11, wherein said reductase is *Kluyveromyces aestuarii*-derived carbonyl reductase.

18. An isolated polypeptide comprising a variant of the amino acid sequence of SEQ ID NO: 2, wherein the residues at position 6 and 256 of SEQ ID NO: 2 are amino acids other than cysteine while the remaining residues are left unchanged, and wherein the polypeptide has increased formate dehydrogenase activity in the presence of an organic solvent in comparison to the protein consisting of the amino acid sequence of SEQ ID NO: 2.

19. An isolated polypeptide comprising a variant of the amino acid sequence of SEQ ID NO: 2, wherein the residue at position 6 is serine, alanine or valine, and the residue at position 256 is serine, alanine or valine while the remaining residues are left unchanged.

20. The polypeptide of claim 19, wherein the residue at position 6 is alanine and the residue at position 256 is valine.

21. The polypeptide of claim 19, wherein the residue at position 6 is alanine and the residue at position 256 is serine.

22. The polypeptide of claim 19, wherein the residue at position 6 is alanine and the residue at position 256 is serine.

23. The polypeptide of claim 19, wherein the residue at position 6 is alanine and the residue at position 256 is alanine.

24. The polypeptide of claim 19, wherein the residue at position 6 is alanine and the residue at position 256 is valine.

25. An isolated polypeptide comprising a variant of the amino acid sequence of SEQ ID NO: 2, wherein the residues at position 6, 146 and 256 of SEQ ID NO: 2 are amino acids other than cysteine while the remaining residues are left unchanged, and wherein the polypeptide has increased formate dehydrogenase activity in the presence of an organic solvent in comparison to the protein consisting of the amino acid sequence of SEQ ID NO: 2.

26. The polypeptide of claim 25, wherein the residue at position 6 is serine, alanine or valine; the residue at position 146 is serine or alanine; and the residue at position 256 is serine, alanine or valine.

27. An isolated polypeptide comprising a variant of the amino acid sequence of SEQ ID NO: 2, wherein the residue at position 6 is serine, alanine or valine; the residue at position 146 is serine or alanine; and the residue at position 256 is serine, alanine or valine while the remaining residues are left unchanged.

28. The polypeptide of claim 27, wherein the residue at position 6 is serine, the residue at position 146 is serine, and the residue at position 256 is serine.

29. The polypeptide of claim 27, wherein the residue at position 6 is alanine, the residue at position 146 is serine, and the residue at position 256 is valine.

30. The polypeptide of claim 27, wherein the residue at position 6 is alanine, the residue at position 146 is alanine, and the residue at position 256 is valine.

31. A method for producing a reduced form of β-nicotinamide adenine dinucleotide from an oxidized form of β-nicotinamide adenine dinucleotide, said method comprising contacting the polypeptide of claim 2 with the oxidized form of β-nicotinamide adenine dinucleotide.

32. A method for producing a reduced form of β-nicotinamide adenine dinucleotide from an oxidized form of β-nicotinamide adenine dinucleotide, said method comprising contacting the polypeptide of claim 3 with the oxidized form of β-nicotinamide adenine dinucleotide.

33. A method for producing a reduced form of β-nicotinamide adenine dinucleotide from an oxidized form of β-nicotinamide adenine dinucleotide, said method comprising contacting the polypeptide of claim 5 with the oxidized form of β-nicotinamide adenine dinucleotide.

34. A method for producing a reduced form of β-nicotinamide adenine dinucleotide from an oxidized form of β-nicotinamide adenine dinucleotide, said method comprising contacting the polypeptide of claim 6 with the oxidized form of β-nicotinamide adenine dinucleotide.

35. A method for producing a reduced form of β-nicotinamide adenine dinucleotide from an oxidized form of β-nicotinamide adenine dinucleotide, said method comprising contacting the polypeptide of claim 7 with the oxidized form of β-nicotinamide adenine dinucleotide.

36. A method for producing a reduced form of β-nicotinamide adenine dinucleotide from an oxidized form of β-nicotinamide adenine dinucleotide, said method comprising contacting the polypeptide of claim 18 with the oxidized form of β-nicotinamide adenine dinucleotide.

37. A method for producing a reduced form of β-nicotinamide adenine dinucleotide from an oxidized form of β-nicotinamide adenine dinucleotide, said method comprising contacting the polypeptide of claim 19 with the oxidized form of β-nicotinamide adenine dinucleotide.

38. A method for producing a reduced form of β-nicotinamide adenine dinucleotide from an oxidized form of β-nicotinamide adenine dinucleotide, said method comprising contacting the polypeptide of claim 25 with the oxidized form of β-nicotinamide adenine dinucleotide.

39. A method for producing a reduced form of β-nicotinamide adenine dinucleotide from an oxidized form of β-nicotinamide adenine dinucleotide, said method comprising contacting the polypeptide of claim 27 with the oxidized form of β-nicotinamide adenine dinucleotide.

40. A method for producing a reduced product from an oxidized substrate, said method comprising the steps of:
  (1) producing a reduced form of β-nicotinamide adenine dinucleotide by the method of claim 31; and
  (2) recovering a reduced product generated by contacting the reduced form of β-nicotinamide adenine dinucleotide of step (1) and an oxidized substrate with a reductase that produces the reduced product from the oxidized substrate in the presence of the reduced form of β-nicotinamide adenine dinucleotide, thereby producing the reduced product.

41. A method for producing a reduced product from an oxidized substrate, said method comprising the steps of:
  (1) producing a reduced form of β-nicotinamide adenine dinucleotide by the method of claim 32; and
  (2) recovering a reduced product generated by contacting the reduced form of β-nicotinamide adenine dinucleotide of step (1) and an oxidized substrate with a reductase that produces the reduced product from the oxidized substrate in the presence of the reduced form of β-nicotinamide adenine dinucleotide, thereby producing the reduced product.

42. A method for producing a reduced product from an oxidized substrate, said method comprising the steps of:
  (1) producing a reduced form of β-nicotinamide adenine dinucleotide by the method of claim 33; and
  (2) recovering a reduced product generated by contacting the reduced form of β-nicotinamide adenine dinucleotide of step (1) and an oxidized substrate with a reductase that produces the reduced product from the oxidized substrate in the presence of the reduced form of β-nicotinamide adenine dinucleotide, thereby producing the reduced product.

43. A method for producing a reduced product from an oxidized substrate, said method comprising the steps of:
  (1) producing a reduced form of β-nicotinamide adenine dinucleotide by the method of claim 34; and
  (2) recovering a reduced product generated by contacting the reduced form of β-nicotinamide adenine dinucleotide of step (1) and an oxidized substrate with a reductase that produces the reduced product from the oxidized substrate in the presence of the reduced form of β-nicotinamide adenine dinucleotide, thereby producing the reduced product.

44. A method for producing a reduced product from an oxidized substrate, said method comprising the steps of:
   (1) producing a reduced form of β-nicotinamide adenine dinucleotide by the method of claim 35; and
   (2) recovering a reduced product generated by contacting the reduced form of β-nicotinamide adenine dinucleotide of step (1) and an oxidized substrate with a reductase that produces the reduced product from the oxidized substrate in the presence of the reduced form of β-nicotinamide adenine dinucleotide, thereby producing the reduced product.

45. A method for producing a reduced product from an oxidized substrate, said method comprising the steps of:
   (1) producing a reduced form of β-nicotinamide adenine dinucleotide by the method of claim 36; and
   (2) recovering a reduced product generated by contacting the reduced form of β-nicotinamide adenine dinucleotide of step (1) and an oxidized substrate with a reductase that produces the reduced product from the oxidized substrate in the presence of the reduced form of β-nicotinamide adenine dinucleotide, thereby producing the reduced product.

46. A method for producing a reduced product from an oxidized substrate, said method comprising the steps of:
   (1) producing a reduced form of β-nicotinamide adenine dinucleotide by the method of claim 37; and
   (2) recovering a reduced product generated by contacting the reduced form of β-nicotinamide adenine dinucleotide of step (1) and an oxidized substrate with a reductase that produces the reduced product from the oxidized substrate in the presence of the reduced form of β-nicotinamide adenine dinucleotide, thereby producing the reduced product.

47. A method for producing a reduced product from an oxidized substrate, said method comprising the steps of:
   (1) producing a reduced form of β-nicotinamide adenine dinucleotide by the method of claim 38; and
   (2) recovering a reduced product generated by contacting the reduced form of β-nicotinamide adenine dinucleotide of step (1) and an oxidized substrate with a reductase that produces the reduced product from the oxidized substrate in the presence of the reduced form of β-nicotinamide adenine dinucleotide, thereby producing the reduced product.

48. A method for producing a reduced product from an oxidized substrate, said method comprising the steps of:
   (1) producing a reduced form of β-nicotinamide adenine dinucleotide by the method of claim 39; and
   (2) recovering a reduced product generated by contacting the reduced form of β-nicotinamide adenine dinucleotide of step (1) and an oxidized substrate with a reductase that produces the reduced product from the oxidized substrate in the presence of the reduced form of β-nicotinamide adenine dinucleotide, thereby producing the reduced product.

49. The method of claim 40, wherein said oxidized substrate is a ketone and said reduced product is an alcohol.

50. The method of claim 41, wherein said oxidized substrate is a ketone and said reduced product is an alcohol.

51. The method of claim 42, wherein said oxidized substrate is a ketone and said reduced product is an alcohol.

52. The method of claim 43, wherein said oxidized substrate is a ketone and said reduced product is an alcohol.

53. The method of claim 44, wherein said oxidized substrate is a ketone and said reduced product is an alcohol.

54. The method of claim 45, wherein said oxidized substrate is a ketone and said reduced product is an alcohol.

55. The method of claim 46, wherein said oxidized substrate is a ketone and said reduced product is an alcohol.

56. The method of claim 47, wherein said oxidized substrate is a ketone and said reduced product is an alcohol.

57. The method of claim 48, wherein said oxidized substrate is a ketone and said reduced product is an alcohol.

58. The method of claim 40, wherein said reductase is *Kluyveromyces aestuarii*-derived carbonyl reductase.

59. The method of claim 41, wherein said reductase is *Kluyveromyces aestuarii*-derived carbonyl reductase.

60. The method of claim 42, wherein said reductase is *Kluyveromyces aestuarii*-derived carbonyl reductase.

61. The method of claim 43, wherein said reductase is *Kluyveromyces aestuarii*-derived carbonyl reductase.

62. The method of claim 44, wherein said reductase is *Kluyveromyces aestuarii*-derived carbonyl reductase.

63. The method of claim 45, wherein said reductase is *Kluyveromyces aestuarii*-derived carbonyl reductase.

64. The method of claim 46, wherein said reductase is *Kluyveromyces aestuarii*-derived carbonyl reductase.

65. The method of claim 47, wherein said reductase is *Kluyveromyces aestuarii*-derived carbonyl reductase.

66. The method of claim 48, wherein said reductase is *Kluyveromyces aestuarii*-derived carbonyl reductase.

\* \* \* \* \*

UNITED STATES PATENT AND TRADEMARK OFFICE
CERTIFICATE OF CORRECTION

PATENT NO. : 6,830,907 B2
DATED : December 14, 2004
INVENTOR(S) : Kazuya Mitsuhashi, Hiroaki Yamamoto and Norihiro Kimoto It is certified that error appears in the above-identified patent and that said Letters Patent is hereby corrected as shown below:

Title page,
Item [56], References Cited, OTHER PUBLICATIONS,
"Slusarczyk et al." second reference delete "*Candida buodinii*" and replace with
-- *Candida boidinii* --.

Column 41,
Line 14, delete "position 6 is alanine" and replace with -- position 6 is valine --.
Line 16, delete "position 6 is alanine" and replace with -- position 6 is serine --.

Signed and Sealed this

Seventh Day of February, 2006

JON W. DUDAS
*Director of the United States Patent and Trademark Office*